US012562246B2

(12) United States Patent
Wang et al.

(10) Patent No.: US 12,562,246 B2
(45) Date of Patent: Feb. 24, 2026

(54) DATA PROCESSING METHOD, DATA PROCESSING APPARATUS, AND HEALTH MANAGEMENT APPARATUS

(71) Applicant: BOE Technology Group Co., Ltd., Beijing (CN)

(72) Inventors: Zhou Wang, Beijing (CN); Zigang Liu, Beijing (CN); Yuan Gao, Beijing (CN); Tongbo Wang, Beijing (CN); Guilong Yang, Beijing (CN); Feng Qi, Beijing (CN); Yang Han, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 544 days.

(21) Appl. No.: 17/772,783

(22) PCT Filed: May 27, 2021

(86) PCT No.: PCT/CN2021/096383
§ 371 (c)(1),
(2) Date: Apr. 28, 2022

(87) PCT Pub. No.: WO2021/249197
PCT Pub. Date: Dec. 16, 2021

(65) Prior Publication Data
US 2022/0383997 A1     Dec. 1, 2022

(30) Foreign Application Priority Data
Jun. 9, 2020    (CN) .......................... 202010519612.7

(51) Int. Cl.
*G16H 10/60*        (2018.01)
*G06F 16/35*        (2025.01)
(Continued)

(52) U.S. Cl.
CPC ............. *G16H 10/60* (2018.01); *G06F 16/35* (2019.01); *G06F 18/22* (2023.01); *G16H 50/30* (2018.01)

(58) Field of Classification Search
CPC ......... G06F 16/35; G06F 18/22; G16H 10/60; G16H 50/30; G16H 15/00
See application file for complete search history.

(56) References Cited

U.S. PATENT DOCUMENTS

| | | | |
|---|---|---|---|
| 10,517,515 B2 | 12/2019 | Newberry | |
| 2015/0317743 A1* | 11/2015 | Flam ....................... | G16Z 99/00 705/4 |
| 2019/0034590 A1 | 1/2019 | Oren et al. | |

FOREIGN PATENT DOCUMENTS

| | | |
|---|---|---|
| CN | 102647369 A | 8/2012 |
| CN | 105590031 A | 5/2016 |

(Continued)

OTHER PUBLICATIONS

Dong et al. "Similarity search for web services." VLDB. vol. 4. 2004. (Year: 2004).*
Li Zonghao et al., Chinese Disaster Rescue Medicine; Tianjing Science and Technology Press; pp. 1079; Jul. 31, 2014.
Wang Yongzhi et al, 3D Geological Modeling Methods and Applications; Central South University Press; pp. 63; Jan. 31, 2018.

(Continued)

*Primary Examiner* — Jay A Morrison
(74) *Attorney, Agent, or Firm* — Banner & Witcoff, Ltd.

(57)         ABSTRACT
A data processing method, a data processing apparatus, and a health management apparatus. The data processing method includes: performing data processing on device-related data from a device associated with a health management apparatus. The data processing apparatus and the health management apparatus can improve the uniformity of memories provided to be associated with the health management apparatus.

20 Claims, 8 Drawing Sheets

(51) Int. Cl.
     *G06F 18/22*     (2023.01)
     *G16H 50/30*     (2018.01)

(56)                    References Cited

FOREIGN PATENT DOCUMENTS

| CN | 105956409 A | 9/2016 |
| CN | 107766504 A | 3/2018 |
| CN | 108024745 A | 5/2018 |
| CN | 108597605 A | 9/2018 |
| CN | 108874928 A | 11/2018 |
| CN | 110019478 A | 7/2019 |
| CN | 110164565 A | 8/2019 |
| CN | 109033439 B | 11/2019 |
| CN | 110767279 A | 2/2020 |

OTHER PUBLICATIONS

Sun Lianyou et al, The Basic Status of Maritime Environmental Resources in the Coastal Waters of Tianjin; Brijing: China Ocean Press; pp. 225; Nov. 30, 2013.

Li Jinping et al, Biomath Fun Talk; Harbin Institute of Technology Press; pp. 24; Jan. 31, 2015.

Douglas W Mapel et al, An Algorithm for the Identification of Undiagnosed COPD Cases Using Administrative Claims Data; Jul. 2006-Aug. 12(6):457-65.

Suhyun Kim et al, A Cluster Analysis of Chronic Obstructive Pulmonary Disease in Dusty Areas Cohort Identified Three Subgroups; BMC Pulm Med. 2017; 17: 209.

Daniel Sanchez-Morillo et al, Use of Predictive Algorithms In-Home Monitoring of Chronic Obstructive Pulmonary Disease and Asthma; Chron Respir Dis. Aug. 2016; 13(3): 264-283.

* cited by examiner

S90

Performing data processing on device-related data originating from a device associated with a health managing apparatus.

Health managing apparatus

Data processing
apparatus

FIG. 19

DATA PROCESSING METHOD, DATA PROCESSING APPARATUS, AND HEALTH MANAGEMENT APPARATUS

CROSS-REFERENCE TO RELATED APPLICATION

The application is a U.S. National Phase Entry of International Application PCT/CN2021/096383 filed on May 27, 2021, designating the United States of America and claiming priority to Chinese Patent Application No. 202010519612.7 filed on Jun. 9, 2020. The present application claims priority to and the benefit of the above-identified applications and the above-identified applications are incorporated by reference herein in their entirety.

TECHNICAL FIELD

At least one embodiments of the present disclosure relates to a data processing method, a data processing apparatus, and a health managing apparatus.

BACKGROUND

With economic development and improvement of living standards, more and more people suffer from chronic diseases of varying degrees. Common chronic disease (or non-communicable disease) mainly includes cardiovascular and cerebrovascular disease, cancer, diabetes, and chronic respiratory disease, etc.; and the cardiovascular and cerebrovascular disease includes hypertension, stroke and coronary heart disease, etc. Data shows that there are more Chinese citizens suffering from chronic disease such as hypertension, diabetes, and dyslipidemia, etc.

SUMMARY

At least one embodiment of the present disclosure discloses a data processing method, comprising: performing data processing on device-related data originating from a device associated with a health managing apparatus.

For example, in at least one example of the data processing method, the performing data processing on device-related data originating from a device associated with a health managing apparatus, comprises: based on information of a first group of keywords involved in template data and information of a second group of keywords involved in the device-related data, acquiring a structural similarity degree between the first group of keywords and the second group of keywords; and transferring at least a portion of the device-related data into the template data based on the structural similarity degree.

For example, in at least one example of the data processing method, the performing data processing on device-related data originating from a device associated with a health managing apparatus, further comprises: receiving the device-related data and the information of the first group of keywords involved in the template data; and the information of the first group of keywords comprises an eigenvector of each keyword of the first group of keywords, and the information of the second group of keywords comprises an eigenvector of each keyword of the second group of keywords.

For example, in at least one example of the data processing method, the performing data processing on device-related data originating from a device associated with a health managing apparatus, further comprises: extracting the second group of keywords and hierarchical information of each keyword of the second group of keywords in the device-related data from the device-related data; generating an eigenvector of each keyword of the second group of keywords based on the second group of keywords and hierarchical information of each keyword of the second group of keywords in the device-related data.

For example, in at least one example of the data processing method, the structural similarity degree between the first group of keywords and the second group of keywords comprises a similarity degree between an eigenvector of each keyword of the first group of keywords and an eigenvector of each keyword of the second group of keywords.

For example, in at least one example of the data processing method, the based on information of a first group of keywords involved in a template data and information of a second group of keywords involved in the device-related data, acquiring a structural similarity degree between the first group of keywords and the second group of keywords, comprises: acquiring the structural similarity degree between the first group of keywords and the second group of keywords by calculating a similarity degree matrix S; and the similarity degree matrix S satisfying an expression below:

$$S = \begin{bmatrix} u_1 v_1 & u_1 v_2 & \cdots & u_1 v_m \\ u_2 v_1 & u_2 v_2 & & u_2 v_m \\ \vdots & \vdots & \ddots & \vdots \\ u_b v_1 & u_b v_2 & \cdots & u_b v_m \end{bmatrix}$$

where $v_1, v_2, \ldots, v_m$ are eigenvectors of the first group of keywords, $u_1, u_2, \ldots, u_b$ are eigenvectors of the second group of keywords, m is a count of keywords in the first group of keywords, and b is a count of keywords in the second group of keywords.

For example, in at least one example of the data processing method, wherein the transferring at least a portion of the device-related data into the template data based on the structural similarity degree, comprises: taking a similarity degree between an eigenvector of each keyword of the second group of keywords and an eigenvector of each keyword of the first group of keywords greater than a preset similarity degree threshold as a relevant similarity degree; taking a keyword belonging to the second group of keywords in two keywords corresponding to each relevant similarity degree as a first keyword, and taking a keyword belonging to the first group of keywords in the two keywords corresponding to each relevant similarity degree as a second keyword; and associating data associated with the first keyword in the device-related data with the second keyword involved in the template data.

For example, in at least one example of the data processing method, the performing data processing on device-related data originating from a device associated with a health managing apparatus, further comprises: receiving an interpolated data set, wherein the interpolated data set comprises at least a portion of data of other objects in a group to which an object corresponding to data to be supplemented belongs; and performing interpolation on the interpolated data set to acquire the data to be supplemented.

For example, in at least one example of the data processing method, the performing data processing on device-related data originating from a device associated with a health managing apparatus, further comprises: calculating a nominal distance between the data to be supplemented and each piece of data in the interpolated data set; and the performing interpolation on the interpolated data set to acquire the data to be supplemented, comprises: performing inverse distance interpolation on the interpolated data set at least based on the nominal distance to acquire the data to be supplemented.

For example, in at least one example of the data processing method, the calculating a nominal distance between the data to be supplemented and each piece of data in the interpolated data set, comprises: calculating a nominal distance between the data to be supplemented and each piece of data in the interpolated data set, based on a time distance and a geographic distance between the data to be supplemented and each piece of data in the interpolated data set.

For example, at least one example of the data processing method further comprises: receiving time information and geographic location information corresponding to each piece of data in the interpolated data set, as well as time information and geographic location information corresponding to the data to be supplemented, wherein the calculating a nominal distance between the data to be supplemented and each piece of data in the interpolated data set, comprises: calculating a time distance between the data to be supplemented and each piece of data in the interpolated data set, based on time information corresponding to each piece of data in the interpolated data set and the time information corresponding to the data to be supplemented; calculating a geographic distance between the data to be supplemented and each piece of data in the interpolated data set, based on geographic information corresponding to each piece of data in the interpolated data set and the geographic information corresponding to the data to be supplemented; and taking a weighted sum of a spatial distance between the data to be supplemented and each piece of data in the interpolated data set and a time distance between the data to be supplemented and each piece of data in the interpolated data set as a nominal distance between the data to be supplemented and each piece of data in the interpolated data set.

For example, at least one example of the data processing method further comprises: receiving a damping item of the group to which the object corresponding to the data to be supplemented belongs, wherein the performing interpolation on the interpolated data set to acquire the data to be supplemented, comprises: performing inverse distance interpolation on the interpolated data set based on the nominal distance and the damping item to acquire the data to be supplemented.

For example, in at least one example of the data processing method, the data to be supplemented $x_p$ satisfies an expression below:

$$x_p = \frac{\sum_{i=1}^{n} \frac{x_i}{d_{pi}^{1.5}}}{\sum_{i=1}^{n} \frac{1}{e_k \cdot d_{pi}^{1.5}}}$$

$x_i$ is an i-th piece of data in the interpolated data set, where i is a positive integer greater than or equal to 1 and less than or equal to n; n is a count of pieces of data in the interpolated data set; $d_{pi}$ is a nominal distance between the data to be supplemented $x_p$ and the i-th piece of data $x_i$ in the interpolated data set; $e_k$ is the damping item of the group to which the object corresponding to the data to be supplemented belongs, k is greater than or equal to 1 and less than or equal to t, and t is a group sequence number of a group to which an object associated with the health managing apparatus belongs.

For example, at least one example of the data processing method further comprises: receiving information of the object associated with the health managing apparatus; acquiring scores of the object associated with the health managing apparatus on a plurality of scoring items based on the information of the object associated with the health managing apparatus and a look-up table; and assigning a group to the object associated with the health managing apparatus based on the scores of the object associated with the health managing apparatus on the plurality of scoring items.

For example, in at least one example of the data processing method, the assigning a group to the object associated with the health managing apparatus based on the scores of the object associated with the health managing apparatus on a plurality of scoring items, comprises: acquiring an overall score of the object associated with the health managing apparatus based on the scores on the plurality of scoring items and weights of the plurality of scoring items; and assigning the group to the object associated with the health managing apparatus based on the overall score.

For example, in at least one example of the data processing method, the acquiring an overall score of the object associated with the health managing apparatus based on the scores on the plurality of scoring items and weights of the plurality of scoring items, comprises: taking a weighted sum of the scores of the object associated with the health managing apparatus on the plurality of scoring items as the overall score of the object associated with the health managing apparatus; and the assigning the group to the object associated with the health managing apparatus based on the overall score, comprises: taking the overall score rounded up as a group sequence number of the object associated with the health managing apparatus.

For example, in at least one example of the data processing method, the information of the object associated with the health managing apparatus comprises objective information and subjective information; at least a portion of the objective information is acquired through monitoring the object associated with the health managing apparatus by a portable medical device or a wearable medical device; and at least a portion of the subjective information is acquired through queries by a medical worker or an electronic questionnaire filled by the object associated with the health managing apparatus.

For example, in at least one example of the data processing method, the plurality of scoring items comprise: age, gender, Body Mass Index, systolic blood pressure, diastolic blood pressure, occupational work intensity, a count of exacerbations, a count of hospitalizations, a count of surgical treatments, normal respiratory rate, normal oxyhemoglobin saturation, mental status and exercise status.

For example, at least one example of the data processing method further comprises: receiving the overall score of the object associated with the health managing apparatus, and outputting pre-warning information in a case where the overall score of the object associated with the health managing apparatus is greater than a score threshold.

For example, in at least one example of the data processing method, the performing data processing on device-related data originating from a device associated with a health managing apparatus, comprises: performing distributed processing on the device-related data originating from the device associated with the health managing apparatus.

At least one embodiment of the present disclosure discloses a data processing apparatus, comprising: a processor and a memory, wherein the memory stores computer program instructions suitable for execution by the processor; and in a case where the computer program instructions are run by the processor, causing the processor to execute a method comprising: performing data processing on device-related data originating from a device associated with a health managing apparatus.

At least one embodiment of the present disclosure discloses a health managing apparatus, comprising the data processing apparatus provided by at least one embodiment of present disclosure.

At least one embodiment of the present disclosure discloses a non-transitory storage medium, having computer program instructions stored thereon; wherein when the computer program instructions are run by a processor, the computer program instructions cause the process to execute a method comprising: performing data processing on device-related data originating from a device associated with a health managing apparatus.

At least one embodiment of the present disclosure discloses another data processing apparatus, comprising a data processing module, wherein the data processing module is configured to perform data processing (e.g., data preprocessing) on device-related data originating from a device associated with the health managing apparatus. For example, the processed data is provided to a memory associated with the health managing apparatus.

For example, in at least one example of the data processing apparatus, the data processing apparatus includes a data transfer module; and the data transfer module includes a structural similarity degree calculating sub-module and a transfer sub-module. The structural similarity degree calculating sub-module is configured for acquiring a structural similarity degree between the first group of keywords and the second group of keywords, based on information of a first group of keywords involved in template data and information of a second group of keywords involved in the device-related data; the transfer sub-module is configured for transferring at least a portion of the device-related data into the template data based on the structural similarity degree.

For example, in at least one example of the data processing apparatus, the data transfer module further includes a first data receiving sub-module, and the first data receiving sub-module is configured for receiving the device-related data and the information of the first group of keywords involved in the template data; and the information of the first group of keywords comprises an eigenvector of each keyword of the first group of keywords, and the information of the second group of keywords comprises an eigenvector of each keyword of the second group of keywords.

For example, in at least one example of the data processing apparatus, the data transfer module further includes an information extracting sub-module and an eigenvector generating sub-module. The information extracting sub-module is configured for acquiring the device-related data from the first data receiving sub-module, and extracting the second group of keywords and hierarchical information of each keyword of the second group of keywords in the device-related data from the device-related data; the eigenvector generating sub-module is configured for generating an eigenvector of each keyword of the second group of keywords based on the second group of keywords and hierarchical information of each keyword of the second group of keywords in the device-related data, and supplying the eigenvector of each keyword of the second group of keywords to the structural similarity degree calculating sub-module.

For example, in at least one example of the data processing apparatus, the structural similarity degree between the first group of keywords and the second group of keywords comprises a similarity degree between an eigenvector of each keyword of the first group of keywords and an eigenvector of each keyword of the second group of keywords.

For example, in at least one example of the data processing apparatus, the structural similarity degree calculating sub-module is configured for acquiring the structural similarity degree between the first group of keywords and the second group of keywords by calculating a similarity degree matrix S; and the similarity degree matrix S satisfying an expression below:

$$S = \begin{bmatrix} u_1v_1 & u_1v_2 & \dots & u_1v_m \\ u_2v_1 & u_2v_2 & & u_2v_m \\ \vdots & \vdots & \ddots & \vdots \\ u_bv_1 & u_bv_2 & \dots & u_bv_m \end{bmatrix}$$

where $v_1, v_2, \dots, v_m$ are eigenvectors of the first group of keywords, $u_1, u_2, u_b$ are eigenvectors of the second group of keywords, m is a count of keywords in the first group of keywords, and b is a count of keywords in the second group of keywords.

For example, in at least one example of the data processing apparatus, transferring at least a portion of the device-related data into the template data based on the structural similarity degree, comprises: taking a similarity degree between an eigenvector of each keyword of the second group of keywords and an eigenvector of each keyword of the first group of keywords greater than a preset similarity degree threshold as a relevant similarity degree; taking a keyword belonging to the second group of keywords in two keywords corresponding to each relevant similarity degree as a first keyword, and taking a keyword belonging to the first group of keywords in the two keywords corresponding to each relevant similarity degree as a second keyword; and associating data associated with the first keyword in the device-related data with the second keyword involved in the template data.

For example, in at least one example of the data processing apparatus, the data processing apparatus further includes a data supplementing module, and the data supplementing module includes a second data receiving sub-module and an interpolation calculating sub-module. The second data receiving sub-module is configured for receiving an interpolated data set, wherein the interpolated data set comprises at least a portion of data of other objects in a group to which an object corresponding to data to be supplemented belongs. The interpolation calculating sub-module is configured for performing interpolation on the interpolated data set to acquire the data to be supplemented.

For example, in at least one example of the data processing apparatus, data supplementing module further includes distance calculating module. The distance calculating module is configured for calculating a nominal distance between the data to be supplemented and each piece of data in the interpolated data set; and the distance calculating module is configured for performing inverse distance interpolation on the interpolated data set at least based on the nominal distance to acquire the data to be supplemented.

For example, in at least one example of the data processing apparatus, the distance calculating module is configured for calculating a nominal distance between the data to be supplemented and each piece of data in the interpolated data set, comprises: calculating a nominal distance between the data to be supplemented and each piece of data in the interpolated data set, based on a time distance and a geographic distance between the data to be supplemented and each piece of data in the interpolated data set.

For example, at least one example of the data processing apparatus, the second data receiving sub-module is further configured for receiving time information and geographic location information corresponding to each piece of data in the interpolated data set, as well as time information and geographic location information corresponding to the data to be supplemented; the distance calculating module is further configured for calculating a time distance between the data to be supplemented and each piece of data in the interpolated data set, based on time information corresponding to each piece of data in the interpolated data set and the time information corresponding to the data to be supplemented; the distance calculating module is further configured for calculating a geographic distance between the data to be supplemented and each piece of data in the interpolated data set, based on geographic information corresponding to each piece of data in the interpolated data set and the geographic information corresponding to the data to be supplemented; and taking a weighted sum of a spatial distance between the data to be supplemented and each piece of data in the interpolated data set and a time distance between the data to be supplemented and each piece of data in the interpolated data set as a nominal distance between the data to be supplemented and each piece of data in the interpolated data set.

For example, at least one example of the data processing apparatus, the second data receiving sub-module is further configured for receiving a damping item of the group to which the object corresponding to the data to be supplemented belongs; and the interpolation calculating sub-module is configured for performing inverse distance interpolation on the interpolated data set based on the nominal distance and the damping item to acquire the data to be supplemented.

For example, in at least one example of the data processing apparatus, the data to be supplemented $x_p$ satisfies an expression below:

$$x_p = \frac{\sum_{i=1}^{n} \frac{x_i}{d_{pi}^{1.5}}}{\sum_{i=1}^{n} \frac{1}{e_k \cdot d_{pi}^{1.5}}}$$

where $x_i$ is an i-th piece of data in the interpolated data set, wherein i is a positive integer greater than or equal to 1 and less than or equal to n; n is a count of pieces of data in the interpolated data set; $d_{pi}$ is a nominal distance between the data to be supplemented $x_p$ and the i-th piece of data $x_i$ in the interpolated data set; $e_k$ is the damping item of the group to which the object corresponding to the data to be supplemented belongs, k is greater than or equal to 1 and less than or equal to t, and t is a group sequence number of a group to which an object associated with the health managing apparatus belongs.

For example, at least one example of the data processing apparatus, the data processing module includes an object grouping module. The object grouping module includes a third data receiving sub-module, a score acquiring sub-module and a grouping sub-module. The third data receiving sub-module is configured for receiving information of the object associated with the health managing apparatus; the score acquiring sub-module is configured for acquiring scores of the object associated with the health managing apparatus on a plurality of scoring items based on the information of the object associated with the health managing apparatus and a look-up table; and the grouping sub-module is configured for assigning a group to the object associated with the health managing apparatus based on the scores of the object associated with the health managing apparatus on the plurality of scoring items.

For example, in at least one example of the data processing apparatus, the grouping sub-module is configured for acquiring an overall score of the object associated with the health managing apparatus based on the scores on the plurality of scoring items and weights of the plurality of scoring items; and assigning the group to the object associated with the health managing apparatus based on the overall score.

For example, in at least one example of the data processing apparatus, the overall score of the object associated with the health managing apparatus is equal to a weighted sum of the scores of the object associated with the health managing apparatus on the plurality of scoring items; and the group sequence number of the object associated with the health managing apparatus is equal to the overall score rounded up.

For example, in at least one example of the data processing apparatus, the information of the object associated with the health managing apparatus comprises objective information and subjective information; at least a portion of the objective information is acquired through monitoring the object associated with the health managing apparatus by a portable medical device or a wearable medical device; and at least a portion of the subjective information is acquired through queries by a medical worker or an electronic questionnaire filled by the object associated with the health managing apparatus.

For example, in at least one example of the data processing apparatus, the plurality of scoring items include: age, gender, Body Mass Index, systolic blood pressure, diastolic blood pressure, occupational work intensity, a count of exacerbations, a count of hospitalizations, a count of surgical treatments, normal respiratory rate, normal oxyhemoglobin saturation, mental status and exercise status.

For example, in at least one example of the data processing apparatus, the data processing module further includes a pre-warning sub-module. The pre-warning sub-module is configured for receiving the overall score of the object associated with the health managing apparatus, and outputting pre-warning information in a case where the overall score of the object associated with the health managing apparatus is greater than a score threshold.

For example, in at least one example of the data processing apparatus, the data processing apparatus further includes a pre-cache module and a post-cache module. The pre-cache module is configured to receive the device-related data generated by a device associated with the health managing apparatus, and supply the device-related data to the data processing module. The post-cache module is configured to receive processed data output by the data processing module, and supply the processed data to the memory of the health managing apparatus For example, in at least one example of the data processing apparatus, the pre-cache module is configured to cooperate with a distributed system to allow the data processing module to perform distributed processing on device-related data generated by the device associated with the health managing apparatus.

BRIEF DESCRIPTION OF THE DRAWINGS

In order to clearly illustrate the technical solutions of the embodiments of the present disclosure, the drawings of the embodiments will be briefly described in the following; it is obvious that the described drawings are only related to some embodiments of the present disclosure and thus are not limitative to the present disclosure.

FIG. 19 is an exemplary block diagram of a health managing apparatus provided by at least one embodiment of the present disclosure.

DETAILED DESCRIPTION

Figure 1:
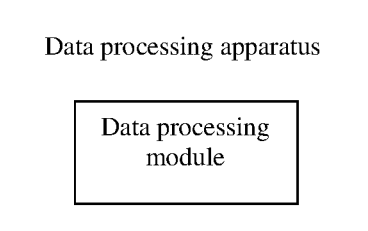
FIG. 1 is an exemplary block diagram of a data processing apparatus provided by at least one embodiment of the present disclosure.

In order to make objects, technical solutions, and advantages of the embodiments of the present disclosure apparent, the technical solutions of the embodiments of the present disclosure will be described in a clearly and fully understandable way in connection with the drawings related to the embodiments of the present disclosure. Apparently, the described embodiments are just a part but not all of the embodiments of the present disclosure. Based on the described embodiments of the present disclosure, those skilled in the art can obtain other embodiment(s), without any inventive work, which should be within the scope of the present disclosure.

Unless otherwise defined, all the technical and scientific terms used herein have the same meanings as commonly understood by one of ordinary skill in the art to which the present disclosure belongs. The terms "first," "second," etc., which are used in the present disclosure, are not intended to indicate any sequence, amount or importance, but distinguish various components. The terms "comprise," "comprising," "include," "including," etc., are intended to specify that the elements or the objects stated before these terms encompass the elements or the objects and equivalents thereof listed after these terms, but do not preclude the other elements or objects. The phrases "connect", "connected", etc., are not intended to define a physical connection or mechanical connection, but may include an electrical connection, directly or indirectly. "On," "under," "right," "left" and the like are only used to indicate relative position relationship, and when the position of the object which is described is changed, the relative position relationship may be changed accordingly.

For example, a word vector technology may be divided into a word vector technology based on statistical methods and a word vector technology based on language models. For example, the word vector technology based on statistical methods may be divided into a word vector technology based on co-occurrence matrix and a word vector technology based on singular value decomposition. For example, in the word vector technology based on language models, the language model generates a word vector by training a Neural Network Language Model (NNLM), and the word vector serves as incidental output of the language model. For example, the word vector technology based on language models includes a word vector technology based on word2vec. For example, word2vec is implemented by means of neural network, by using a skip-gram model and Continuous Bag of Words (CBOW). For example, a skip-gram model uses a word as an input to predict a context around it; and the CBOW model uses a context of a word as an input to predict the word itself. For example, the related art may be referred to for training methods of skip-gram and CBOW, and no details will be repeated here.

An inventor of the present disclosure notices in the study that, with development of technologies, a large number of portable devices and wearable devices are adopted by patients, so the amount of data received by a managing apparatus for managing the devices used by the patients increases, which may lead to failure of the managing apparatus to receive all the data, especially in a period when the devices used by the patients upload the data centrally (e.g., a period when the devices are connected with WIFI after the patients return home from work at night). In addition, since the above-described portable devices and wearable devices may involve a plurality of manufacturers, formats and contents of the data generated by the devices used by the patients, keywords involved in the data, and frequencies of device-collecting devices may not be uniform, which may lead to problems that data mismatched with a database associated with the managing apparatus is difficult to be directly used by a subsequent data processing module.

For example, at present, more and more medical big data systems have become complicated for data processing with respect to intelligent medical treatment needs during medical treatment of chronic respiratory disease, and subsequently put forward new requirements for quality of data inbound; on the other hand, in the era of mobile medical care, a large number of portable and wearable devices enter homes of ordinary patients, such devices generate a large amount of data, but current medical big data systems lack means of receiving and preprocessing such data.

Embodiments of the present disclosure provide a data processing method, a data processing apparatus, and a health managing apparatus. The data processing apparatus includes a data processing module. The data processing module is configured to perform data processing (e.g., data preprocessing) on device-related data originating from a device associated with the health managing apparatus. The processed data is supplied, for example, to a memory associated with the health managing apparatus. For example, by using the data processing module configured to perform data processing on the device-related data originating from the device associated with the health managing apparatus, uniformity supplied to the memory associated with the health managing apparatus may be improved.

The data processing apparatus provided by the embodiments of the present disclosure will be described below in a non-limiting manner through several examples and embodiments; as described below, different features in these specific examples and embodiments may be combined with each other without conflict, so as to obtain new examples and embodiments, and these new examples and embodiments also belong to the protection scope of the present disclosure.

FIG. 1 is an exemplary block diagram of a data processing apparatus provided by at least one embodiment of the present disclosure. As shown in FIG. 1, the data processing apparatus includes a data processing module. The data processing module is configured to perform data processing (e.g., data preprocessing) on device-related data originating from a device associated with a health managing apparatus, and to supply the processed data to a memory associated with the health managing apparatus or a data analyzing module or data processing module included in the health managing apparatus.

For example, the device associated with (e.g., bound to) the health managing apparatus allows the data generated by the above-described device (e.g., raw data) or the processed data based on data obtained from the above-described device-related data to be supplied (e.g., directly or indirectly) to the memory associated with the health managing apparatus.

For example, the device-related data originating from the device associated with the health managing apparatus refers to data generated by the device associated with the health managing apparatus and received by the data processing module.

For example, the memory associated with the health managing apparatus refers to a memory (or a database carried by the memory) for storing the data received by the health managing apparatus or the data generated by the health managing apparatus.

For example, the device associated with the health managing apparatus may be set according to actual application requirements, which will not be specifically limited by at least one embodiment of the present disclosure.

For example, the device associated with the health managing apparatus may be a detecting device or a treating device. For example, the detecting device is configured to monitor vital-sign data (e.g., blood pressure, oxyhemoglobin saturation, respiratory rate, body temperature, etc.) of the user using the device. For example, the detecting device may be a spirometer, a pulse oximeter, a ventilator, a non-invasive multi-parameter detector, a blood pressure monitor, a smart bracelet, a forehead thermometer, or the like. For example, the treating device is used in treatment and rehabilitation of an object. For example, an oxygenerator may be used to administer oxygen therapy to a patient using the oxygenerator.

For example, the device associated with the health managing apparatus may be a portable medical device, a wearable medical device, a stationary device. For example, the portable medical device may be a device that belongs to an object (a patient) or a device that belongs to a hospital and is used by a doctor when he/she goes out for diagnosis and treatment. For example, the wearable medical device may be a device worn by an object (e.g., a patient) for monitoring vital-signs of the object. For example, a stationary device is an instrument that is placed in a fixed location (e.g., a hospital, a rehabilitation center, or a nursing home).

For example, each piece of device-related data (e.g., raw data) may include identification information and substantive information. For example, the identification information of the device associated with the health managing apparatus may be at least one of an identifier (e.g., a serial number) of the device and an identifier of a device user. For example, the identifier of the device is selected from the serial number of the device, a platform serial number of the device (e.g., a number of the device in a health management platform), and an internal number (e.g., a number of the device in a database associated with the memory). For example, the identifier of the device user is selected from identity information of the device user (e.g., an ID number or a passport number), a mobile phone number, a WeChat ID, and an Alipay number.

For example, the substantive information includes at least one of detection data and usage data. For example, in a case where the device associated with the health managing apparatus is a detecting device, the substantive information may be vital-sign data of the object using the detecting device acquired by the detecting device. For example, in a case where the device associated with the health managing apparatus is a spirometer, the substantive information may include lung capacity. For example, in a case where the device associated with the health managing apparatus is a treating device or a rehabilitating device, the substantive information may be at least one type of setting parameter data of the treating device or the rehabilitating device and time data when the object uses the treating device or the rehabilitating device. For example, in a case where the device associated with the health managing apparatus is a ventilator, the substantive information may include at least one of ventilation frequency of the ventilator and time when the object uses the ventilator.

For example, because devices associated with the health managing apparatus involve a plurality of types of devices, formats and time frequencies (corresponding to frequencies at which the devices collect data) of device-related data generated by different devices associated with the health managing apparatus may be different from each other. For example, a format of the device-related data originating from the device associated with the health managing apparatus may be different from a data storage format and time frequency of the database carried by the memory associated with the health managing apparatus.

For example, the format of the data includes: the number of keywords involved in the data, fields of keywords involved in the data, specific names of keywords involved in the data (keywords with a same field), and structures of the data (e.g., hierarchies at which keywords involved in the data are located in the data). For example, the keywords involved in data refer to characters used to indicate meaning of numerical values in the data.

For example, the data storage format of the database carried by the memory associated with the health managing apparatus may be {"device identifier": " ", "substantive information": {"respiratory rate": " ", "oxyhemoglobin saturation": " ", "systolic blood pressure": " "}}; in this case, the keywords involved in the data storage format of the database include: "device identifier", "respiratory rate", "oxyhemoglobin saturation", "systolic blood pressure", and hierarchies of the above-described four keywords are respectively level 1, level 2, level 2 and level 2.

For example, the device-related data may be {"device identifier": "01010202", "substantive information": {"respiratory rate": "15", "oxyhemoglobin saturation": "95%"}}; in this case, the keywords involved in device-related data include: "device identifier", "respiratory rate" and "oxyhemoglobin saturation", and hierarchies of the above-described three keywords are respectively level 1, level 2 and level 2. Therefore, the number of keywords involved in the device-related data is less than the number of keywords involved in the data inbound format of the database.

For another example, the device-related data may be {"device identifier: "01010202", "respiratory rate": "15", "oxyhemoglobin saturation": "95%", "systolic blood pressure": "100"}; in this case, the keywords involved in the device-related data include: "device identifier", "respiratory rate", "oxyhemoglobin saturation" and "systolic blood pressure", and hierarchies of the above-described four keywords are respectively level 1, level 1, level 1 and level 1. Therefore, hierarchies of some keywords involved in the device-related data is inconsistent with hierarchies of the corresponding keywords (e.g., "respiratory rate") involved in the data storage format of the database.

For another example, the device-related data may be {"device identification sign": "01010202", "substantive information": {"respiratory rate": "15", "oxyhemoglobin saturation": "95%", "systolic blood pressure": "100"}}; in this case, the keywords involved in the device-related data include: "device identification sign", "respiratory rate", "oxyhemoglobin saturation" and "systolic blood pressure", and levels of the above-described four keywords are respectively level 1, level 2, level 2 and level 2. Therefore, specific names of some keywords involved in the device-related data (e.g., "device identification sign" and "device identifier") are different.

For another example, the device-related data may be {"device identifier": "01010202", "substantive information": {"respiratory rate": "15", "oxyhemoglobin saturation": "95%", "weight": "50 kg"}}; in this case, the keywords involved in the device-related data include: "device identifier", "respiratory rate", "oxyhemoglobin saturation"

and "weight", and hierarchies of the above-described four keywords are respectively level 1, level 2, level 2 and level 2. Therefore, fields for some keywords (e.g., "systolic blood pressure" and "weight") involved in the device-related data are different.

For example, a predetermined data format and a time frequency may be the data storage format and the time frequency of the database carried by the memory associated with the health managing apparatus. For another example, the predetermined data format and the time frequency may also be the data format and the time frequency adopted by most devices among the plurality of devices associated with the health managing apparatus.

For example, the time frequency of the device-related data is inconsistent with the predetermined time frequency, including at least one of situations below: the time frequency of the device-related data generated by the device (e.g., the frequency at which the device collects data) is inconsistent with the predetermined time frequency; the time frequency of the device-related data generated by the device is consistent with the predetermined time frequency, but because of data missing or defect problems in a data transmission process, the time frequency of the device-related data transmitted to the memory associated with the health managing apparatus is inconsistent with the predetermined time frequency.

For example, the above-described data missing or defect includes missing an entire piece of data and missing values corresponding to some fields in a piece of data.

For example, the device-related data generated by the device over a predetermined period (e.g., 10 minutes) includes {"device identification sign": "01010202", "substantive information": {"respiratory rate": "15", "oxyhemoglobin saturation": "95%", "systolic blood pressure": "100"}} and {"device identification sign": "01010202", "substantive information": {"respiratory rate": "16", "oxyhemoglobin saturation": "96%", "systolic blood pressure": "102"}}, but in a case where the data received by the data processing module is only {"device identification sign": "01010202", "substantive information": {"respiratory rate": "15", "oxyhemoglobin saturation": "95%", "systolic blood pressure": "100"}}, there is a problem of missing the entire piece of data; in this case, it will lead to inconsistency of the time frequency of the device-related data with the predetermined time frequency in a specific period.

For another example, the device-related data generated by the device in a predetermined period (e.g., 10 minutes) includes {"device identification sign": "01010202", "substantive information": {"respiratory rate": "15", "oxyhemoglobin saturation": "95%", "systolic blood pressure": "100"}} and {"device identification sign": "01010202", "substantive information": {"respiratory rate": "16", "oxyhemoglobin saturation": "96%", "systolic blood pressure": "102"}}, but the data received by the data processing module is only {"device identification sign": "01010202", "substantive information": {"respiratory rate": "15", "oxyhemoglobin saturation": "95%", "systolic blood pressure": "100"}} and {"device identification sign": "01010202", "substantive information": {"respiratory rate": "16", "oxyhemoglobin saturation": "96%", "systolic blood pressure": " "}}, then the above-described second piece of data has the problem of missing some data; in this case, it will lead to inconsistency of the time frequency of the data in some fields ("systolic blood pressure") of the device-related data with the predetermined time frequency in a specific period.

For example, data processing (e.g., data pre-processing) performed on the device-related data may be at least one item of unifying a format of the device-related data with the predetermined data format and unifying a time frequency of the device-related data with the predetermined time frequency.

For example, by using the data processing module to perform data processing on the device-related data originating from the device associated with the health managing apparatus, uniformity of the data supplied to the memory associated with the health managing apparatus may be improved, which thus facilitates performing subsequent data processing and analysis on the data, and facilitates improving a utilization rate of the data.

Figure 2:
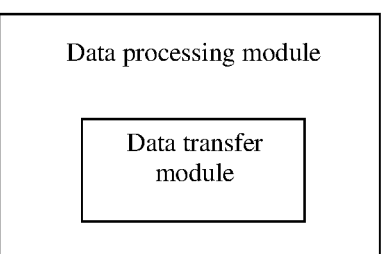
FIG. 2 is an exemplary block diagram of a first example of a data processing module provided by at least one embodiment of the present disclosure.

FIG. 2 is an exemplary block diagram of a first example of a data processing module provided by at least one embodiment of the present disclosure. For example, as shown in FIG. 2, the data processing module includes a data transfer module.

Figure 3:
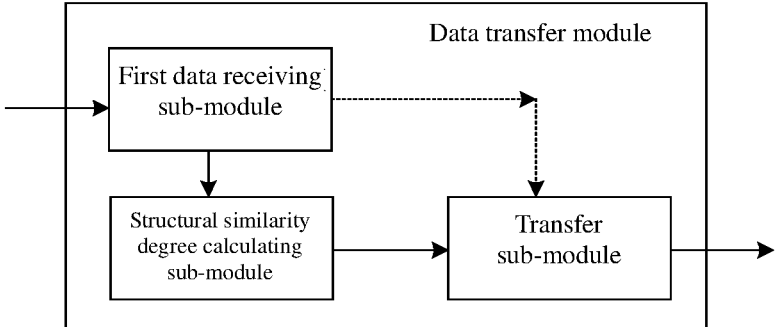
FIG. 3 is an exemplary block diagram of a data transfer module provided by at least one embodiment of the present disclosure.
Figure 4:
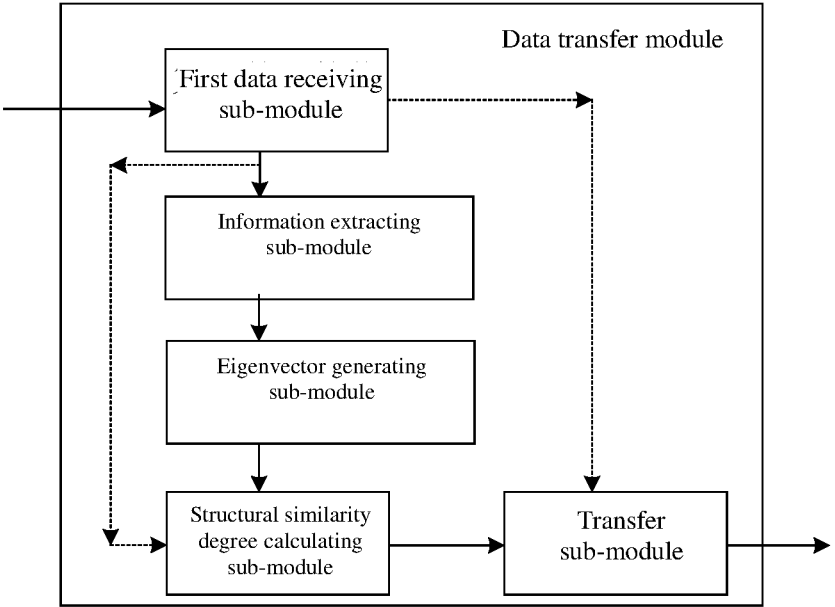
FIG. 4 is another exemplary block diagram of a data transfer module provided by at least one embodiment of the present disclosure.

FIG. 3 is an exemplary block diagram of a data transfer module provided by at least one embodiment of the present disclosure. FIG. 4 is another exemplary block diagram of a data transfer module provided by at least one embodiment of the present disclosure. For example, as shown in FIG. 3 and FIG. 4, the data transfer module includes a structural similarity degree calculating sub-module and a transfer sub-module.

For example, the structural similarity degree calculating sub-module is configured to acquire a structural similarity degree between a first group of keywords and a second group of keywords based on information of the first group of keywords involved in template data and information of the second group of keywords involved in the device-related data.

For example, a data format and a time frequency of the template data may be a predetermined data format and time frequency. For example, the data format and the time frequency of the template data may be consistent with a data storage format and a time frequency of the database carried by the memory associated with the health managing apparatus. For another example, the data format and the time frequency of the template data may be consistent with a data format and a time frequency adopted by most devices of the plurality of devices associated with the health managing apparatus.

For example, the template data may be data that does not include a specific numerical value or empty data having a data format. For example, the template data may be {"device identifier": " ", "substantive information": {"respiratory rate": " ", "oxyhemoglobin saturation": " ", "systolic blood pressure": " "}}.

For example, information of a keyword is an eigenvector of the keyword. For example, the eigenvector VE of the keyword may be calculated by using a text feature extraction algorithm f, based on a text t of the keyword and a hierarchy L in which the keyword is located in the data. For example, the eigenvector VE may be represented by using an expression below: VE=f(t, L). For example, the text feature extraction algorithm f may be a word vector technology based on word2vec or other suitable algorithms. For example, the related art may be referred to for the text feature extraction algorithm f, and no details will be repeated here.

For example, by making the eigenvector of the keyword be obtained by calculating based on the text t of the keyword and the hierarchy L in which the keyword is located in the data, an application scope of the data transfer module may be improved. For example, the data transfer module is made not only applicable to data with fixed or known data structures.

For example, the information of the first group of keywords includes an eigenvector of each keyword of the first group of keywords; the information of the second group of keywords includes an eigenvector of each keyword of the second group of keywords.

For example, as shown in FIG. 3 and FIG. 4, the data transfer module further includes a first data receiving sub-module. For example, the first data receiving sub-module is configured to receive the device-related data.

For example, the first data receiving sub-module is configured to obtain necessary data from an initial data source (streaming data) of the data processing apparatus.

For example, as shown in FIG. 4, the data transfer module further includes an information extracting sub-module and an eigenvector generating sub-module.

For example, the information extracting sub-module is configured to acquire the device-related data from the first data receiving sub-module, and extract the second group of keywords and hierarchical information of each keyword of the second group of keywords in the device-related data from the device-related data.

For example, the second group of keywords and the hierarchical information of each keyword of the second group of keywords in the device-related data may be extracted from the device-related data by a method below.

For example, the raw data may be unpacked into list data based on corresponding field criteria provided by a supplier of the device associated with the health managing apparatus. For example, assuming that the supplier of the device adopts the j son format as the transmission format, and the transmission data follows the http protocol, the unpacking process is to extract a packet content from a data stream packaged by the http protocol, and then convert the corresponding fields (e.g., the patient's name and the patient's COPD aggravation times) (i.e., header keywords) into list format data.

For example, other related technologies may also be adopted to extract the second group of keywords and the hierarchical information of each keyword of the second group of keywords in the device-related data from the device-related data, and no details will be repeated here.

For example, the eigenvector generating sub-module is configured to, for each keyword of the second group of keywords, generate an eigenvector of the keyword of the second group of keywords based on the second group of keywords and the hierarchical information, and supply the eigenvector of the keyword of the second group of keywords to the structural similarity degree calculating sub-module. For example, the eigenvector generating sub-module is configured to, for each keyword of the second group of keywords, generate the eigenvector of the keyword of the second group of keywords, based on the hierarchical information of the keyword of the second group of keywords in the device-related data, by using the above-described text feature extraction algorithm.

In one example, the first data receiving sub-module is further configured to receive information of the first group of keywords involved in the template data, and supply the information of the first group of keywords to the structural similarity degree calculating sub-module. For example, by making the first data receiving sub-module directly receive the information of the first group of keywords involved in the template data, and supply the information of the first group of keywords to the structural similarity degree calculating sub-module, computational complexity of the structural similarity degree calculating sub-module may be reduced, especially when the amount of data received by the memory associated with the health managing apparatus is great.

In another example, the first data receiving sub-module is further configured to receive the first group of keywords involved in the template data and hierarchical information of each keyword of the first group of keywords in the template data; in this case, the eigenvector generating sub-module is further configured to, for each keyword of the first group of keywords, generate an eigenvector of the keyword of the first group of keywords based on the first group of keywords and hierarchical information of the keyword of the first group of keywords in the template data, and to supply the eigenvector of the keyword of the first group of keywords to the structural similarity degree calculating sub-module.

In still another example, the first data receiving sub-module is further configured to receive the template data; in this case, the information extracting sub-module is further configured to obtain the template data from the first data receiving sub-module, and extract the first group of keywords and hierarchical information of each keyword of the first group of keywords in the template data from the template data; the eigenvector generating sub-module is further configured to, for each keyword of the first group of keywords, generate an eigenvector of the keyword of the first group of keywords based on the first group of keywords and hierarchical information of the keyword of the first group of keywords in the template data, and to supply the eigenvector of the keyword of the first group of keywords to the structural similarity degree calculating sub-module.

For example, the structural similarity degree between the first group of keywords and the second group of keywords includes a similarity degree between an eigenvector of each keyword of the first group of keywords and an eigenvector of each keyword of the second group of keywords. For example, the eigenvectors of the first group of keywords are $v_1$, $v_2$, . . . , $v_m$, the eigenvectors of the second group of keywords are $u_1$, $u_2$, . . . , $u_b$, m is the number of keywords in the first group of keywords, and b is the number of keywords in the second group of keywords. For example, a similarity degree between an eigenvector of each keyword of the first group of keywords and an eigenvector of each keyword of the second group of keywords includes $u_1v_1$, $u_1v_2$, . . . $u_1v_m$, $u_2v_1$, $u_2v_2$, . . . $u_2v_m$, $u_bv_1$, $u_bv_2$, . . . $u_bv_m$. That is to say, the structural similarity degree between the first group of keywords and the second group of keywords includes m*b similarity degrees, and one of the m*b similarity degrees is a similarity degree between any two keywords, and one of the any two keywords is from the first group of keywords, and the other one of the any two keywords is from the second group of keywords.

For example, by calculating a similarity degree between an eigenvector of each keyword of the first group of keywords and an eigenvector of each keyword of the second group of keywords as the structural similarity degree, an application scope of the data transfer module may be improved. For example, the data transfer module may be made applicable to data having an unknown data format.

For example, the structural similarity degree calculating sub-module is configured to acquire the structural similarity degree between the first group of keywords and the second group of keywords by calculating a similarity degree matrix S below; the similarity degree matrix S satisfies an expression below:

$$S = \begin{bmatrix} u_1v_1 & u_1v_2 & \dots & u_1v_m \\ u_2v_1 & u_2v_2 & & u_2v_m \\ \vdots & \vdots & \ddots & \vdots \\ u_bv_1 & u_bv_2 & \dots & u_bv_m \end{bmatrix}$$

For example, the structural similarity degree between the first group of keywords and the second group of keywords is acquired by calculating a similarity degree matrix S below, which may reduce computational complexity of the subsequent transfer sub-module. For example, the similarity degree matrix S may be obtained by performing matrix arrangement on the similarity degree between an eigenvector of each keyword of the first group of keywords and an eigenvector of each keyword of the second group of keywords.

For example, a cosine similarity degree may be used to calculate a value of each element $u_iv_j$ in the similarity degree matrix S, where i is greater than or equal to 1 and less than or equal to b, and j is greater than or equal to 1 and less than or equal to m. For example, when two vectors (e.g., $u_i$ and $v_j$) have a same orientation, the cosine similarity degree of the two vectors (i.e., the value of the element $u_iv_j$) has a value of 1; when an included angle between the two vectors is 90°, the cosine similarity degree of the two vectors has a value of 0; when the two vectors point toward completely opposite directions, the cosine similarity degree of the two vectors is −1; so the cosine similarity degree (a cosine value) of the two vectors is between −1 and 1, and the greater the cosine similarity (cosine value) of two vectors, the closer the two vectors are. Correspondingly, two sub-data corresponding to the two vectors have a higher similarity degree. For example, the value of the cosine similarity degree is −1, which indicates that the two vectors are negatively correlated. For example, values of all elements in the vector corresponding to the first sub-data and values of all elements in the vector corresponding to the second sub-data may be positive; in this case, the cosine similarity degree between the vector corresponding to the first sub-data and the vector corresponding to the second sub-data is between 0 to 1.

For example, a value of each element in the similarity degree matrix S may be calculated by using an expression below:

$$u_iv_j = \cos(u_i, v_j) = \frac{u_i^T \cdot v_j}{\|u_i\| \times \|v_j\|}$$

For example, matrix arrangement may be performed on the similarity degree between an eigenvector of each keyword of the first group of keywords and an eigenvector of each keyword of the second group of keywords to obtain the similarity degree matrix S, and then a value of each element in the similarity degree matrix S is calculated. For another example, a value of the similarity degree between an eigenvector of each keyword of the first group of keywords and an eigenvector of each keyword of the second group of keywords may be calculated firstly, and then matrix arrangement is performed on the calculated values of similarity degrees to obtain the calculated similarity degree matrix S.

For example, the transfer sub-module is configured to transfer at least a portion of the device-related data into the template data based on the structural similarity degree. For example, transferring at least a portion of the device-related data into the template data based on the structural similarity degree includes: taking a similarity degree between an eigenvector of each keyword of the second group of keywords and an eigenvector of each keyword of the first group of keywords greater than a preset similarity degree threshold as a relevant similarity degree; taking a keyword belonging to the second group of keywords in two keywords corresponding to each relevant similarity degree as a first keyword, and taking a keyword belonging to the first group of keywords in the two keywords corresponding to each relevant similarity degree as a second keyword; and associating the data associated with the first keyword in the device-related data with the second keyword involved in the template data.

For example, the associating the data associated with the first keyword in the device-related data with the second keyword involved in the template data refers to transferring the data associated with the first keyword in the device-related data to a field of the template data that corresponds to the second keyword.

For example, the preset similarity degree threshold may be set according to actual application requirements, which will not be specifically limited by the embodiment of the present disclosure.

A specific implementation mode of the data transfer module is exemplarily described below in conjunction with an example.

For example, assuming that the device-related data includes {"patient name": "Zhang San", "age": "28", "weight": "66"}; the template data is {"name of patient": "Li Si", "age": "48", "substantive information": {"blood pressure": "42", "weight": "55"}}; and data transfer may be performed based on steps below:

Firstly, acquiring the first group of keywords involved in the template data (i.e., "name of patient", "age", "blood pressure", "weight") and hierarchical information of each keyword of the first group of keywords in the template data (i.e., level 1, level 1, level 2, and level 2); acquiring the second group of keywords involved in the device-related data (i.e., "patient name", "age", "weight"), and hierarchical information of each keyword of the second group of keywords in the template data (i.e., level 1, level 1, and level 1).

Secondly, acquiring the eigenvectors of the first group of keywords involved in the template data and the eigenvectors of the second group of keywords. For example, the eigenvectors $v_1$, $v_2$, $v_3$, $v_4$ of the first group of keywords respectively represent "name of patient", "age", "blood pressure", "weight", and $v_1=[1, 0, 0.1]$, $v_2=[0, 0, 2]$, $v_3=[0.45, 0.27, 0.41]$, $v_4=[3.1, 0.2, 0.3]$. For example, the eigenvectors $u_1$, $u_2$, $u_3$ of the second group of keywords respectively represent "patient name", "age", "weight", and $u_1=[1,0,0]$, $u_2=[0,0,2]$ and $u_3=[0,3,0]$.

Thirdly, the similarity degree matrix S is calculated.

$$S = \begin{bmatrix} u_1v_1 & u_1v_2 & u_1v_3 & u_1v_4 \\ u_2v_1 & u_2v_2 & u_2v_3 & u_2v_4 \\ u_3v_1 & u_3v_2 & u_3v_3 & u_3v_4 \end{bmatrix} = \begin{bmatrix} 0.99 & 0 & 0.68 & 0.06 \\ 0.09 & 1.0 & 0.62 & 0.10 \\ 0 & 0 & 0.41 & 0.99 \end{bmatrix}$$

Fourthly, finding an element in the similarity degree matrix S whose value is greater than the preset similarity degree threshold, and taking the element in the similarity degree matrix S whose value is greater than the preset similarity degree threshold as the relevant similarity degree. For example, the preset similarity degree threshold may be set to 0.95.

For example, after executing the operation, a matrix $S_{>0.95}$ below may be obtained. An element in the matrix $S_{>0.95}$ with a value of 1 corresponds to the element in the similarity degree matrix S whose value is greater than the preset similarity degree threshold. Therefore, the relevant similarity degree in the similarity degree matrix S includes $u_1v_1=0.99$, $u_2v_2=1$ and $u_3v_4=0.99$.

$$S_{>0.95} = \begin{bmatrix} 1 & 0 & 0 & 0 \\ 0 & 1 & 0 & 0 \\ 0 & 0 & 0 & 1 \end{bmatrix}.$$

Fifthly, finding two keywords involved in the relevant similarity degree, and determining the first keyword and the second keyword among the two keywords. The two keywords involved in the relevant similarity degree $u_1v_1=0.99$ are "patient name ($v_1$, the second keyword)" and "name of patient ($u_1$, the first keyword)"; the two keywords involved in the relevant similarity degree $u_2v_2=1$ are "age ($v_2$, the second keyword)" and "age ($u_2$, the first keyword)"; and the two keywords involved in the relevant similarity degree $u_3v_4=0.99$ are "weight ($v_4$, the second keyword)" and "weight ($u_3$, the first keyword)". For example, the two keywords involved in the relevant similarity degree may be identified as similar fields and may be merged.

Sixthly, associating the data associated with the first keyword in the device-related data with the second keyword involved in the template data. For example, the associated template data is as follows: {"name of patient": "Li Si; Zhang San", "age": "48; 28", "substantive information": {"blood pressure": "42; [ ]", "weight": "55; 66"}}.

For example, based on the calculated structural similarity degree, the transfer sub-module transfers the corresponding value into the corresponding field to complete a cross-keyword mutual transfer. For example, calculating the structural similarity degree is to allow similar fields in different criteria of different devices to be merged and disambiguated. For example, values corresponding to a field "patient name" of a manufacturer A and a field "name of patient" of a manufacturer B are values of the keywords. For example, "patient name" corresponds to "Zhang San". For example, the transferring mode may be merging keywords of two data formats into one keyword, and serializing the corresponding values; for example, "patient name"-"Zhang San", "name of patient"-"Li Si" in the original data format may be merged as "patient name"-"Zhang San", "patient name"-"Li Si". For example, the data transfer module may effectively convert data in different formats to a same storage form smoothly, and improve uniformity of inbound patient data (in the database).

For example, the data transfer module may also be referred to as a cross-keyword mutual transfer module. For example, by calculating the structural similarity degree, the cross-keyword mutual transfer module may facilitate transferring according to the semantic structural relevance. For example, by calculating the structural similarity degree, data of a corresponding keyword may be converted into a corresponding field for storage based on the above-described structural similarity degree, and data corresponding to keywords having a same substantive meaning expressed in different languages may be mutually transferred, which improves uniformity of inbound patient data.

Figure 5:
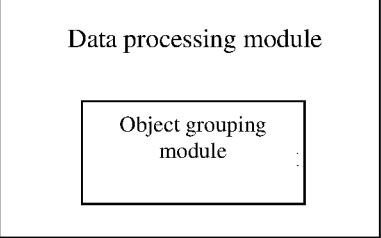
FIG. 5 is an exemplary block diagram of a second example of a data processing module provided by at least one embodiment of the present disclosure.

FIG. 5 is an exemplary block diagram of a second example of a data processing module provided by at least one embodiment of the present disclosure. As shown in FIG. 5, the data processing module includes an object grouping module.

Figure 6:
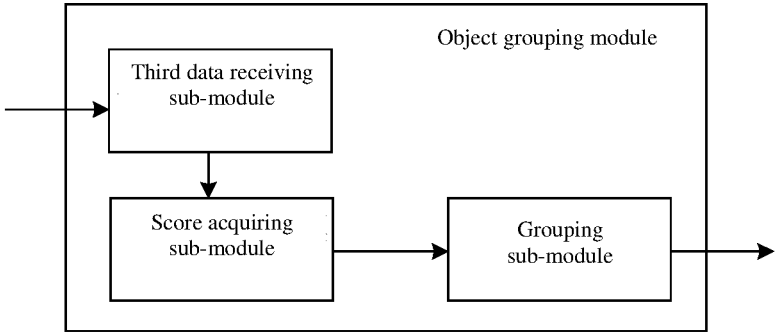
FIG. 6 is an exemplary block diagram of a data transfer module provided by at least one embodiment of the present disclosure.

FIG. 6 is an exemplary block diagram of a data transfer module provided by at least one embodiment of the present disclosure. As shown in FIG. 6, the object grouping module includes a third data receiving sub-module, a score acquiring sub-module and a grouping sub-module.

For example, the third data receiving sub-module is configured to receive information of an object associated with the health managing apparatus. For example, the information of the object associated with the health managing apparatus includes objective information and subjective information.

For example, at least a portion of the objective information is acquired through monitoring the object associated with the health managing apparatus by a portable medical device (e.g., a portable medical device owned by a patient) or a wearable medical device (e.g., a wearable medical device worn by a patient). For example, by allowing at least a portion of the objective information to be acquired through monitoring the object associated with the health managing apparatus by the portable medical device or the wearable medical device, most recent vital-sign data of the object associated with the health managing apparatus may be acquired, thereby allowing to promptly remind the object associated with the health managing apparatus and a doctor who supplies diagnosis and treatment services for the object associated with the health managing apparatus when a condition of the object associated with the health managing apparatus deteriorates or aggravates. In addition, by allowing at least a portion of the objective information to be acquired through monitoring the object associated with the health managing apparatus by the portable medical device or the wearable medical device, a grouping result output by the object grouping module may also be promptly updated when a condition of the object associated with the health managing apparatus deteriorates or aggravates, so as to improve accuracy of a calculation result of the module for data processing by using the grouping result output by the object grouping module.

For example, the subjective information may be obtained by at least one of modes below: queries by a medical worker (queries and confirmations via a remote video system); information (e.g., by filling in an electronic questionnaire) obtained by an object terminal (e.g., on a patient side; for example, a WeChat applet) that matches the health managing apparatus when the object associated with the health managing apparatus uses the object terminal for the first time; update through refilling the electronic questionnaire by the object associated with the health managing apparatus when a situation changes.

For example, information received by the third data receiving sub-module is related to a type of disease suffered by the object associated with the health managing apparatus. For example, with respect to Chronic Obstructive Pulmonary Disease (COPD), the information of the object associated with the health managing apparatus received by the third data receiving sub-module includes: any one or any combination of age, gender, height and weight (or Body Mass Index (BMI)), systolic blood pressure, diastolic blood pressure, occupation work intensity, the number of exacerbations, the number of hospitalizations, the number of surgical treatments, normal respiratory rate, normal oxyhemoglobin saturation, mental state and exercise state.

For example, height, weight, blood pressure, respiratory rate, oxyhemoglobin saturation, etc. may be obtained through one or more measurements by a portable medical device or a wearable medical device. For example, prior to collecting information of the object associated with the health managing apparatus, the object may be made aware that information will be collected.

For example, the score acquiring sub-module is configured to acquire scores of the object associated with the health managing apparatus on a plurality of scoring items based on the information of the object associated with the health managing apparatus and a look-up table.

For example, specific forms of the plurality of scoring items and the look-up table are related to a type of disease suffered by the object associated with the health managing apparatus. For example, in at least one example of the data processing module, the plurality of scoring items include: age, gender, Body Mass Index (BMI), systolic blood pressure, diastolic blood pressure, occupational work intensity, the number of exacerbations (the number of exacerbations of a specified disease), the number of hospitalizations, the number of surgical treatments, normal respiratory rate, normal oxyhemoglobin saturation, mental status and exercise status.

For example, automated grouping of the object associated with the health managing apparatus may be implemented by acquiring scores of the object associated with the health managing apparatus on a plurality of scoring items based on the information about the object associated with the health managing apparatus and the look-up table. In addition, the scores of the object associated with the health managing apparatus on a plurality of scoring items may more intuitively indicate an abnormality degree of the object on a specified scoring item. Therefore, it is favorable for a medical worker to perform result back-checking based on the look-up table, and further it is favorable for a medical worker to give feedback on a match degree between score distribution in the look-up table and actual medical practice.

For example, the plurality of scoring items and the look-up table may adopt a non-negative scoring method, that is, if the object is normal on the scoring item, the object is scored as 0 on the scoring item; and the greater the score of the object on the scoring item, the more abnormal the object is on the scoring item. For example, by using the non-negative scoring method, negative scores may be avoided, which may improve reliability of calculation results.

For example, Table 1 is referred to for an example of a COPD look-up table. For example, the look-up table shown in Table 1 adopts a quantitative scoring mechanism, formulated based on existing clinical observation, which is simple in criteria, uniform, and very easy to implement.

TABLE 1

| | look-up table for COPD | | | | | | | | |
|---|---|---|---|---|---|---|---|---|---|
| Corresponding points | 3 | 2 | 1 | 0 | 1 | 2 | 3 | 4 | 5 |
| 1. Age (years) | <7 | 7-11 | 12-19 | 20-25 | | | | | |
| 2. Gender | | | | Female | Male | | | | |
| 3. BMI | | <17 | 17-18.4 | 18.5-24 | 25-29 | 30-34 | 35-40 | >40 | |
| 4. Systolic blood pressure (mmHg) | | <110 | 110-120 | 120-130 | 140-150 | 160-170 | >170 | | |
| 5. Diastolic blood pressure (mmHg) | | <72 | 72-79 | 80-86 | 87-90 | >90 | | | |

TABLE 1-continued

| | | | | look-up table for COPD | | | | | |
|---|---|---|---|---|---|---|---|---|---|
| Corresponding points | 3 | 2 | 1 | 0 | 1 | 2 | 3 | 4 | 5 |
| 6. Occupational work intensity | | easy | relieved | normal | stressful | high-intensity | overdraft | | |
| 7. The number of COPD exacerbations | | | | 0 | 1 | 2 | 3-4 | 5-6 | >6 |
| 8. The number of hospitalizations | | | | 0 | 1-2 | 3-6 | >6 | | |
| 9. The number of surgical treatments | | | | 0 | 1 | 2 | 3-4 | >4 | |
| 10. Normal respiratory rate (times/10 seconds) | | <7 | 7 | 8 | 9-13 | 13-15 | 16-20 | 21-30 | >30 |
| 11. Normal oxyhemoglobin saturation (%) | <40 | 40-49 | 50-64 | 65-95 | 96-105 | 106-110 | 111-125 | 126-135 | >135 |
| 12. Mental status | | | | Concentrated | Un-concentrated | | Delusional. | | Un-responsive |
| 13. Exercise status | Bed-ridden | Never | Occasionally | Normal | Often | Vigorous | | | |

For example, the grouping sub-module is configured to assign a group to the object associated with the health managing apparatus based on the scores of the object associated with the health managing apparatus on a plurality of scoring items.

For example, the grouping sub-module is configured to acquire an overall score of the object associated with the health managing apparatus based on the scores on the plurality of scoring items and weights of the plurality of scoring items.

For example, a score of the object associated with the health managing apparatus on an i-th scoring item is $y_i$, where, i is greater than or equal to 1 and less than or equal to c, and c is the number of the plurality of scoring items. For example, with respect to the COPD look-up table shown in Table 1, c is equal to 13. For example, a weight of the i-th scoring item among the plurality of scoring items is $w_{fi}$.

For example, the overall score of the object associated with the health managing apparatus is equal to a weighted sum of the scores of the object associated with the health managing apparatus on the plurality of scoring items. For example, the overall score Sc of the object associated with the health managing apparatus may be expressed by using an expression below.

$$Sc = \sum_{i=1}^{c} \frac{w_{fi} y_i}{c}$$

For example, the grouping sub-module is further configured to assign a group to the object associated with the health managing apparatus based on the overall score. For example, a group number of the object associated with the health managing apparatus is equal to the overall score rounded up. For example, when the overall score of the specified object is 1.2, the number of the group to which the specified object belongs is 2. For example, with respect to the above-described COPD example, the object associated with the health managing apparatus may be categorized into 6 sub-groups, namely, group 0, group 1, group 2, group 3, group 4, and group 5.

For example, by acquiring the overall score of the object associated with the health managing apparatus based on the scores on the plurality of scoring items and weights of the plurality of scoring items, personalization factors of the object (e.g., the patient) as well as personalization factors of medical treatment may be taken into account.

For example, there are significant differences in medical resources of different hospitals, and such differences will have a great impact on a treatment plan of the object, for example, shortage of beds may significantly reduce the number of hospitalizations. For example, with respect to the COPD look-up table shown in Table 1, a total of 13 weight coefficients from $w_{f1}$ to $w_{f13}$ may be set sequentially according to an actual situation of a medical institution serving the patient. For example, weight coefficients may be used to adaptively adjust a reference baseline. For example, $w_{f8}$ may be appropriately adjusted according to actual bed supply and the number of diagnosis and treatments in a hospital to better fit a current diagnosis and treatment plan of the hospital. For example, based on our existing data experience, a sum of a weight of a 10-th scoring item and a weight of an 11-th scoring item may be set to a value not lower than 45% to improve quality (e.g., accuracy) of grouping.

For example, by acquiring the overall score of the object associated with the health managing apparatus based on the scores on the plurality of scoring items and weights of the plurality of scoring items, flexible modification may be performed according to medical practice criteria of various regions, so as to improve stability and extensibility of grouping.

Figure 7:
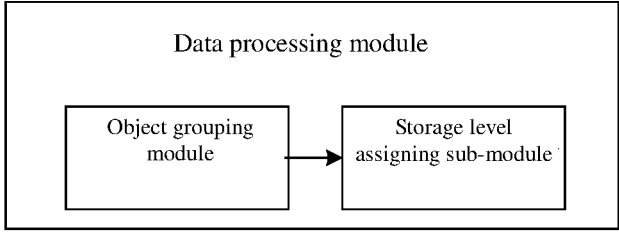
FIG. 7 is an exemplary block diagram of a third example of a data processing module provided by at least one embodiment of the present disclosure.

FIG. 7 is an exemplary block diagram of a third example of a data processing module provided by at least one embodiment of the present disclosure. As shown in FIG. 7, the data processing module includes an object grouping module and a storage level assigning sub-module. For example, the relevant embodiments may be referred to for a specific implementation mode of the object grouping module, and no details will be repeated here.

For example, the storage level assigning sub-module is configured to classify the device-related data corresponding to the object associated with the managing apparatus at least based on the grouping result output by the object grouping module (e.g., a group of the specified object), and assign a processor that matches the classification result for the device-related data corresponding to the object associated with the managing apparatus according to the classification result. For example, high-level data may be placed in a high-speed memory (e.g., cache), medium-level data may be placed in a medium-speed memory (e.g., random access memory), and low-level data may be placed in a low-speed memory in (e.g., a read-only memory or a fixed memory).

For example, because the group of the object represents severity of the object's condition, the group of the object may also be used to indicate importance of data of the object and a predicted value of query frequency, and therefore, before storing the data, the device-related data corresponding to the object associated with the managing apparatus is classified at least according to the group of the specified object, and a processor that matches the classification result is assigned for the device-related data corresponding to the object associated with the managing apparatus according to the classification result, which may speed up query of important data and high-frequency data. Correspondingly, the object associated with the health managing apparatus and the doctor who supplies diagnosis and treatment services for the object associated with the health managing apparatus may be promptly reminded when a condition of the object associated with the health managing apparatus deteriorates or aggravates, so that use experience of the object (e.g., the patient) and the doctor who use the above-described health managing apparatus may be improved.

For example, the storage level assigning sub-module is configured to classify the device-related data corresponding to the object associated with the managing apparatus, at least based on the grouping result output by the object grouping module (e.g., the group of the specified object), storage space that the device-related data corresponding to the specified object needs to occupy, importance degree of the device-related data corresponding to the specified object, and query frequency of past data of the specified object.

For example, by adopting a patient weighted grouping mechanism, the storage level assigning sub-module may be allowed to generate an autonomous caching decision policy based on an importance degree (a predicted value) and a query frequency (a predicted value) for the device-related data generated by the device associated with the managing apparatus; caching recent high-frequency data may accelerate a query speed and an analysis speed, promptness of a pre-warning sub-module (referring to FIG. 8) may be improved, an write operation on important low-frequency data may be selectively executed, database communication efficiency may be improved, and important data are highly reliable and applicable.

Figure 8:
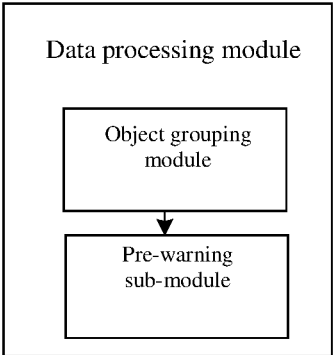
FIG. 8 is an exemplary block diagram of a fourth example of a data processing module provided by at least one embodiment of the present disclosure.

FIG. 8 is an exemplary block diagram of a fourth example of a data processing module provided by at least one embodiment of the present disclosure. As shown in FIG. 8, the data processing module includes an object grouping module and a pre-warning sub-module. For example, the pre-warning sub-module is configured to receive the overall score of the object associated with the health managing apparatus supplied by the grouping sub-module, and output pre-warning information when the overall score of the object associated with the health managing apparatus is greater than a score threshold. For example, the score threshold may be set according to actual application requirements, which will not be specifically limited by the embodiment of the present disclosure. For example, the score threshold may be set to a fixed value (a numerical value indicating that the condition is moderately severe); for example, the score threshold may be set to a variable value. For example, the score threshold may be a rounded-up value of the object's score value prior to the current calculation. For example, by making the data processing module include the object grouping module and the pre-warning sub-module, the object associated with the health managing apparatus and the doctor who supplies diagnosis and treatment services for the object associated with the health managing apparatus may be promptly reminded when a condition of the object associated with the health managing apparatus deteriorates or aggravates, so that use experience of the object (e.g., the patient) and the doctor who use the above-described health managing apparatus may be improved.

In some examples, the data processing module may include an object grouping module, a storage level assigning sub-module, and a pre-warning sub-module at a same time; the relevant embodiments may be referred to for specific implementation modes of the object grouping module, the storage level assigning sub-module, and the pre-warning sub-module, and no details will be repeated here.

Figure 9:
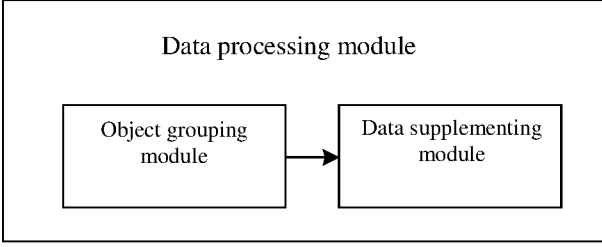
FIG. 9 is an exemplary block diagram of a fifth example of a data processing module provided by at least one embodiment of the present disclosure.

FIG. 9 is an exemplary block diagram of a fifth example of a data processing module provided by at least one embodiment of the present disclosure. As shown in FIG. 9, the data processing module includes an object grouping module and a data supplementing module. For example, the relevant embodiments may be referred to for a specific implementation mode of the object grouping module, and no details will be repeated here.

It should be noted that, in some examples, the data processing module may not include the object grouping module, in this case, the data supplementing module directly receives grouping results of a plurality of object associated with the health managing apparatus from the database or the memory associated with the health managing apparatus.

Figure 10:
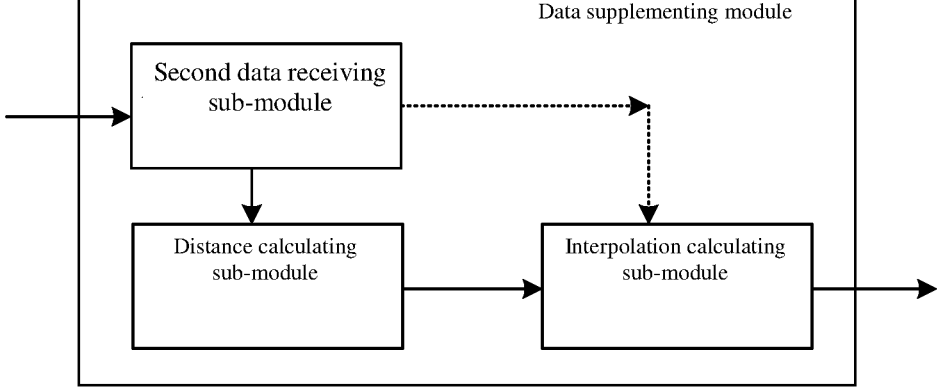
FIG. 10 is an exemplary block diagram of a data supplementing module shown in FIG. 9.
Figure 11:
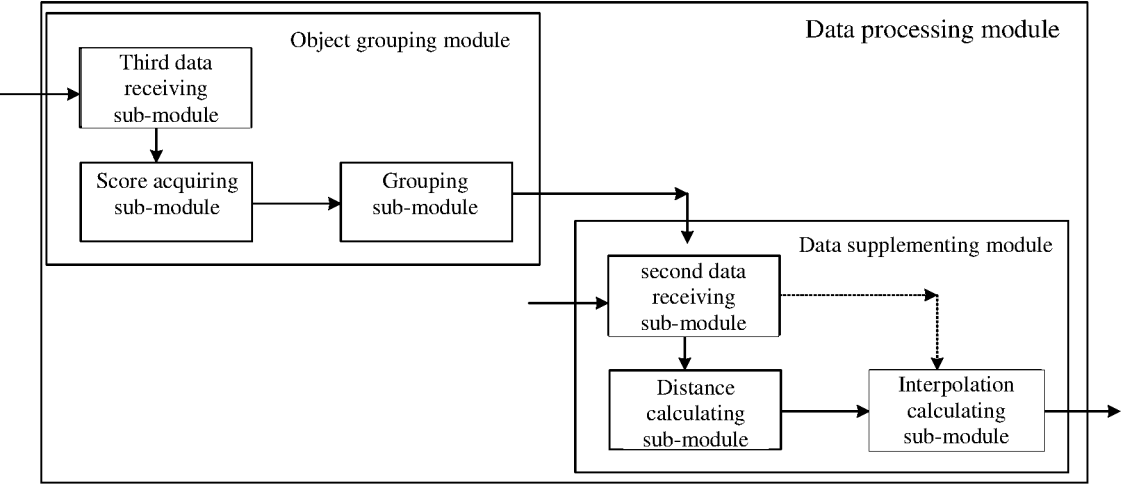
FIG. 11 is another exemplary block diagram of a fifth example of a data processing module provided by at least one embodiment of the present disclosure.

FIG. 10 is an exemplary block diagram of the data supplementing module shown in FIG. 9; and FIG. 11 is another exemplary block diagram of a fifth example of a data processing module provided by at least one embodiment of the present disclosure. As shown in FIG. 10 and FIG. 11, the data supplementing module includes a second data receiving sub-module and an interpolation calculating sub-module.

For example, the second data receiving sub-module is configured to receive an interpolated data set, and the interpolated data set includes at least a portion of data of other objects in the group to which the object corresponding to data to be supplemented belongs. For example, the interpolated data set may include data of all objects except the object corresponding to the data to be supplemented among the plurality of objects in the group to which the object corresponding to the data to be supplemented belongs. For example, a field of a keyword of each piece of data in the interpolated data set is substantially the same as a field of a keyword of the data to be supplemented.

For example, in the interpolated data set, a plurality of pieces of data are in one-to-one correspondence with a plurality of objects, that is, the number of pieces of the plurality of pieces of data is equal to the number of objects other than the first object in the group to which the first object (the object corresponding to the data to be supplemented) belongs. For another example, in the interpolated data set, each object is related to a plurality of pieces of data; in this case, the number of pieces of data is greater than the number of objects other than the first object in the group to which the first object (the object corresponding to the data to be supplemented) belongs.

For example, firstly, the data transfer module may be used to unify data formats of the device-related data corresponding to a plurality of objects, and then it may be judged whether the device-related data corresponding to the specified object has a data missing problem by checking whether a value of the device-related data corresponding to a specified keyword at specified time is empty. For example, the above-described data missing problem may be caused by data transfer or data acquisition. For another example, the above-described data missing problem may be caused by a low frequency of data collection by the device.

For example, the data to be supplemented may be data corresponding to some keywords in the device-related data. For example, in a case where the device-related data generated at a specified device includes {"device identification sign": "01010202", "substantive information": {"respiratory rate": "15", "oxyhemoglobin saturation": "95%", "systolic blood pressure": "100"}}, and the data received by the data supplementing module includes {"device identification sign": "01010202", "substantive information": {"respiratory rate": "15", "oxyhemoglobin saturation": "95%", "systolic blood pressure": " "}}, it may be determined that the data corresponding to the keyword "systolic blood pressure" in the device-related data has a missing problem; correspondingly, if the object corresponding to the data to be supplemented (e.g., the first object) is located in group 3, the second data receiving sub-module may be used to receive data corresponding to the keyword "systolic blood pressure" in the device-related data corresponding to all objects in group 3 except the first object.

For example, the interpolated data set includes n pieces of data, and x, is an i-th piece of data in the interpolated data set, where i is a positive integer greater than or equal to 1 and less than or equal to n.

For example, the interpolation calculating sub-module is configured to perform interpolation on the interpolated data set to acquire the data to be supplemented. For example, through acquiring the data to be supplemented by using at least a portion of the data of other objects in the group to which the object corresponding to the data to be supplemented belongs, credibility of the data to be supplemented may be improved.

For example, as shown in FIG. 10 and FIG. 11, the data supplementing module further includes a distance calculating module; the distance calculating module is configured to calculate a nominal distance between the data to be supplemented and each piece of data in the interpolated data set, and supply the nominal distance to the interpolation calculating sub-module; and the interpolation calculating sub-module is configured to perform inverse distance interpolation on the interpolated data set at least based on the nominal distance to acquire the data to be supplemented.

For example, an inventor of the present disclosure notices that, as compared with historical data of the object corresponding to the data to be supplemented, data in the device-related data of other objects in the group to which the object corresponding to the data to be supplemented belongs that has a closer nominal distance to the data to be supplemented is closer to the data to be supplemented; and therefore, the data to be supplemented may be acquired by performing inverse distance interpolation on the interpolated data set at least based on the nominal distance, so that the data to be supplemented may be made more credible and accurate.

For example, the distance calculating module is configured to calculate a nominal distance between the data to be supplemented and each piece of data in the interpolated data set based on a time distance and a geographic distance between the data to be supplemented and each piece of data in the interpolated data set. For example, as compared with calculating a nominal distance between the data to be supplemented and each piece of data in the interpolated data set only based on the time distance or the geographic distance between the data to be supplemented and each piece of data in the interpolated data set, by calculating a nominal distance between the data to be supplemented and each piece of data in the interpolated data set based on the time distance and the geographic distance between the data to be supplemented and each piece of data in the interpolated data set, the nominal distance between the data to be supplemented and each piece of data in the interpolated data set may be more accurate.

For example, the second data receiving sub-module is further configured to receive time information (e.g., timestamp) and geographic location information corresponding to each piece of data in the interpolated data set, as well as time information (e.g., timestamp) and geographic location information corresponding to the data to be supplemented.

For example, the time information (e.g., the timestamp) and the geographic location information corresponding to the data to be supplemented may be acquired based on a predetermined data collection frequency of the device as well as the time information (e.g., the timestamp) and the geographic location information (presumably obtained) corresponding to the device-related data adjacent to the data to be supplemented.

For example, the geographic location information corresponding to the above-described data may be at least one item of home address and work address provided by the object during registration, location of the device when the device used by the object generates the data, and location of the device when the device used by the object uploads the data.

For example, the time information corresponding to the above-described data may be at least one item of time when the device used by the object generates the data and time when the device used by the object uploads the data.

For example, the distance calculating module is further configured to calculate a time distance between the data to be supplemented and each piece of data in the interpolated data set based on time information corresponding to each piece of data in the interpolated data set and the time information corresponding to the data to be supplemented; and the distance calculating module is further configured to calculate a geographic distance between the data to be supplemented and each piece of data in the interpolated data set based on geographic information corresponding to each piece of data in the interpolated data set and the geographic information corresponding to the data to be supplemented.

For example, based on geographic location information between the patient corresponding to the data to be supplemented and the patient corresponding to the interpolated data, the number of intersections on a shortest street between the two patients may be determined, and the above-described number of intersections on the shortest street is taken as the geographic distance between the two patients. For example, time difference between a time stamp of data of the patient corresponding to the data to be supplemented and a time stamp of data of the patient corresponding to the interpolated data may be taken as the time distance between the two patients For example, the nominal distance between the data to be supplemented and each piece of data in the interpolated data set is equal to a weighted sum of the spatial distance (i.e., geographic distance) between the data to be supplemented and each piece of data in the interpolated data set and the time distance between the data to be supplemented and each piece of data in the interpolated data set. The nominal distance between the data to be supplemented $x_p$ and the i-th piece of data in the interpolated data set is $d_{pi}$.

For example, weight coefficients ws and wt may be respectively set for the spatial distance and the time distance. For example, the weight coefficients ws and wt may be set based on medical practice and statistical survey results for a specified disease. For example, by taking the weighted sum of the spatial distance between the data to be supplemented and each piece of data in the interpolated data set and the time distance between the data to be supplemented and each piece of data in the interpolated data set as the nominal distance between the data to be supplemented and each piece of data in the interpolated data set, an application range of the distance calculating module and the data supplementing module as well as accuracy of the output results may be improved.

For example, the second data receiving sub-module is further configured to receive a damping item of the group to which the object corresponding to the data to be supplemented belongs; and the interpolation calculating sub-module is configured to perform inverse distance interpolation on the interpolated data set based on the nominal distance and the damping item to acquire the data to be supplemented.

For example, the data to be supplemented $x_p$ satisfies an expression below:

$$x_p = \frac{\sum_{i=1}^{n} \frac{x_i}{d_{pi}^{1.5}}}{\sum_{i=1}^{n} \frac{1}{e_k \cdot d_{pi}^{1.5}}}$$

$e_k$ is the damping item of the group to which the object corresponding to the data to be supplemented belongs, k is greater than or equal to 1 and less than or equal to t, and t is a group sequence number of a group to which an object associated with the health managing apparatus belongs.

For example, by performing inverse distance interpolation on the interpolated data set based on the nominal distance and the damping item to acquire the data to be supplemented, an interpolation degree (a value) of the data to be supplemented corresponding to the objects in a group with greater disease severity may be increased, so as to improve validity (e.g., measure validity) of the data obtained by interpolation.

For example, damping items $e_k$ of different groups may have different values. For example, the values of damping items $e_k$ of different groups may be set based on medical practice and statistical survey results for a specified disease.

For example, an implementation mode of a data supplementing module provided by at least one embodiment of the present disclosure will be exemplarily described below in conjunction with an example.

For example, assuming that patient A in the first group has systolic blood pressure data missing at time point t1 (16.00 on Jun. 3, 2020), the first group has three other patients besides patient A, and systolic blood pressure data of the above-described three patients at time point t1 is respectively 110, 120 and 130. For example, nominal distances between patient A and the above-described three patients may be obtained based on the distance calculating module, and the nominal distances between patient A and the above-described three patients are respectively 1, 2 and 3. For example, the damping item $e_k$ of the first group is set to 0.1. In this case, the interpolated data $x_p$ may be calculated by an expression below.

30

$$x_p = \frac{\frac{110}{1^{1.5}} + \frac{120}{2^{1.5}} + \frac{130}{3^{1.5}}}{\frac{1}{0.1 \times 1^{1.5}} + \frac{1}{0.1 \times 2^{1.5}} + \frac{1}{0.1 \times 3^{1.5}}} = 144$$

For example, if the damping item $e_k$ is set to 1.1, the interpolation degree may be amplified, and the value of $x_p$ is 127.

It should be noted that, the data to be supplemented may be data corresponding to all keywords in the device-related data. For example, in a case where device-related data generated at a specified device for a predetermined period includes {"device identification sign": "01010202", "substantive information": {"respiratory rate": "15", "oxyhemoglobin saturation": "95%", "systolic blood pressure": "100"}} and {"device identification sign": "01010202", "substantive information": {"respiratory rate": "18", "oxyhemoglobin saturation": "94%", "systolic blood pressure": "98"}}, but the data received by the data supplementing module only includes {"device identification sign": "01010202", "substantive information": {"respiratory rate": "15", "oxyhemoglobin saturation": "95%", "systolic blood pressure": "100"}}, it may be determined that there is a missing problem in the data corresponding to all keywords in the device-related data; in this case, data corresponding to each keyword may be respectively acquired by using the above-described data supplementing module and the corresponding method.

For example, inverse distance interpolation may be performed on the missing data (due to a transfer problem, a data collection problem, etc.) and data with different frequencies according to living geographic location information provided by the patient when registering in the health managing apparatus, as well as the geographic location information and the time stamp information returned by a mobile device.

For example, the data processing apparatus further includes a pre-cache module (not shown) and a post-cache module (not shown). The pre-cache module is configured to receive device-related data generated by a device associated with the health managing apparatus, and supply the device-related data to the data processing module; and the post-cache module is configured to receive processed data output by the data processing module, and supply the processed data to the memory of the health managing apparatus.

For example, the pre-cache module is configured to cooperate with a distributed system to allow the data processing module to perform distributed processing on device-related data generated by the device associated with the health managing apparatus.

In some examples, the data processing module includes a data transfer module, an object grouping module, and a data supplementing module; and the data processing apparatus includes a data processing module, a pre-cache module and a post-cache module.

For example, the modules and the sub-modules involved in at least one embodiment of the present disclosure may be implemented by software, firmware, hardware, and any combination thereof, for example, the hardware includes a server, a Field Programmable Gate Array (FPGA), or the like.

The data processing apparatus provided by at least one embodiment of the present disclosure will be exemplarily described below in conjunction with the examples shown in FIG. 12 to FIG. 15.

Figure 12:
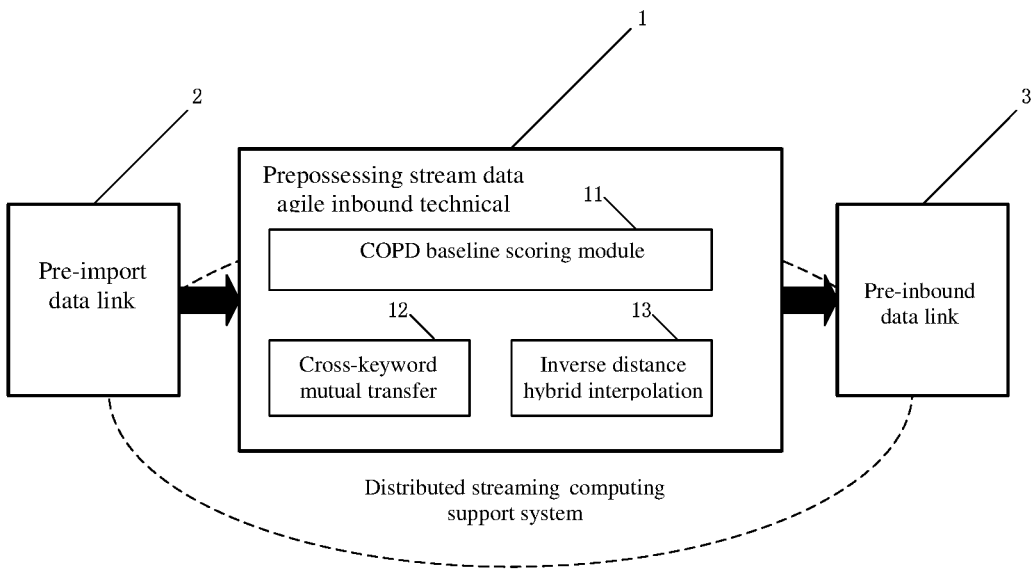
FIG. 12 is an exemplary block diagram of a data agile inbound technical system provided by at least one embodiment of the present disclosure.

At least one embodiment of the present disclosure also provides a data agile inbound technical system 1. FIG. 12 is an exemplary block diagram of a data agile inbound technical system 1 provided by at least one embodiment of the present disclosure.

For example, as shown in FIG. 12, the data agile inbound technical system 1 includes a COPD baseline scoring module 11, an inverse distance hybrid interpolation module 12 and a cross-keyword mutual transfer module 13.

For example, the COPD baseline scoring module 11, the inverse distance hybrid interpolation module 12, and the cross-keyword mutual transfer module 13 may be respectively implemented by the object grouping module, the data supplementing module and the data transfer module shown in FIG. 1 to FIG. 11; and therefore, the examples shown in FIG. 1 to FIG. 11 may be referred to for specific implementation modes of the COPD baseline scoring module 11, the inverse distance hybrid interpolation module 12 and the cross-keyword mutual transfer module 13 as described above.

For example, the COPD baseline scoring module performs reasonable scoring mainly based on basic information (including past medical history) provided by the patient, and performing heterogeneous grouping on the patient, which is favorable for performing group processing of mobile data on the same.

For example, the inverse distance hybrid interpolation module performs hybrid interpolation on the basis of the foregoing COPD baseline scoring module according to the distribution of nominal distances of patients in the group (including baseline conditions, geographic distribution, etc.); in an interpolation algorithm, new data points may be deduced within a range though known, discrete data points, to improve discrepancies caused by data missing and different measurement frequencies.

For example, the cross-keyword mutual transfer module is mainly configured to normalize and transfer discrepancy items of mobile data transferred by different patients because of the device used, the usage methods, etc., to allow for unified data to be obtained.

For example, the above-described data agile inbound technical system 1 may provide an efficient and convenient database inbound storage and processing solution for mobile data collected by mobile devices worn by patients with chronic obstructive pulmonary disease.

For example, as shown in FIG. 12, the data agile inbound technical system may also use a pre-data link cache 2 as an import end of the entire system. The cache may efficiently store the mobile data that has been poured into the system for a period of time, and promptly supply the data to a subsequent processing module according to the FIFO (first-in, first-out) rule (in coordination with the distributed system, FIFO may improve consistency of transfer and storage, keeping data synchronized), so that the mobile data may enter the system, for example, in real time, which prevents data omission. Internal data preprocessing thereof is completed by the above three modules operating collaboratively. After data preprocessing is completed, the cleaned mobile data is imported (e.g., imported via a post-data link 3) into a subsequent analyzing system. For example, because the data is sharded and listed by timestamp, the system uses a distributed pool processing system (i.e., adopts thread pool design), and takes a thread as a minimum scheduling unit, which may speed up parallelism. For example, after preprocessing each piece of data, it is processed by a post-inbound program and enters into the database. For example, the system may efficiently implement the whole process of preprocessing the mobile data and the mobile data entering the database.

For example, by using the pre/post-data link for caching, an efficient FIFO cache may be maintained, which may effectively receive excess streaming data input and prevent data missing.

For example, by using the distributed pool processing mechanism, sharding the streaming data according to time slices, and allocating to a distributed computing pool for preprocessing, real-time computing performance of the system may be improved to provide robustness of the system.

Figure 13:
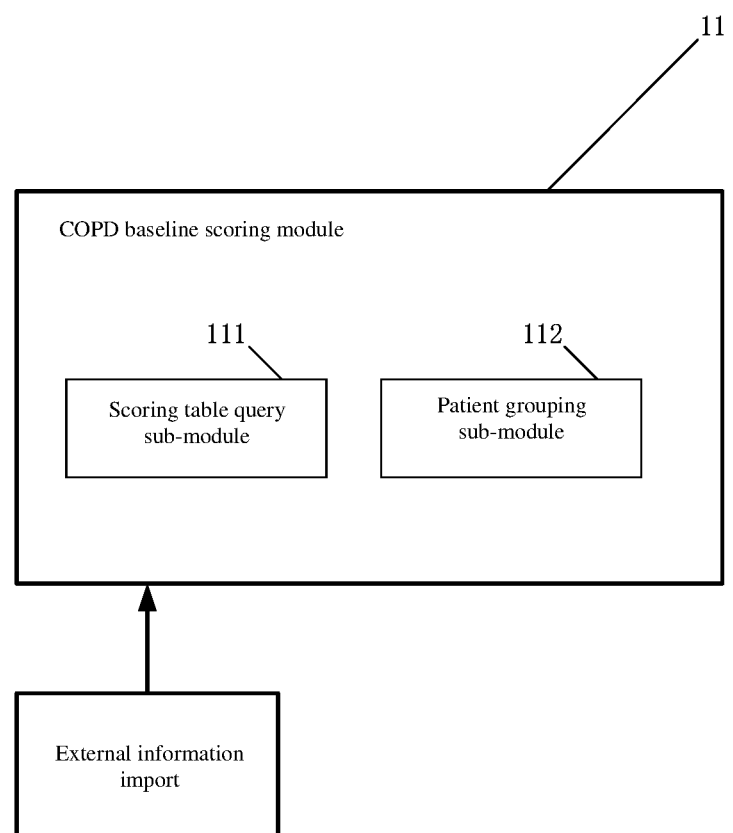
FIG. 13 is an exemplary block diagram of a COPD baseline scoring module of the data agile inbound technical system shown in FIG. 12.

FIG. 13 is an exemplary block diagram of a COPD baseline scoring module of the data agile inbound technical system 1 shown in FIG. 12. For example, as shown in FIG. 13, the COPD baseline scoring module 11 includes a scoring table query sub-module 111 and a patient grouping sub-module 112.

For example, the scoring table query sub-module 111 and the patient grouping sub-module 112 may be respectively implemented by the score acquiring sub-module and the grouping sub-module shown in FIG. 6. Therefore, the example shown in FIG. 6 may be referred to for specific implementation modes of the scoring table query sub-module 111 and patient grouping sub-module 112 as described above.

Figure 14:
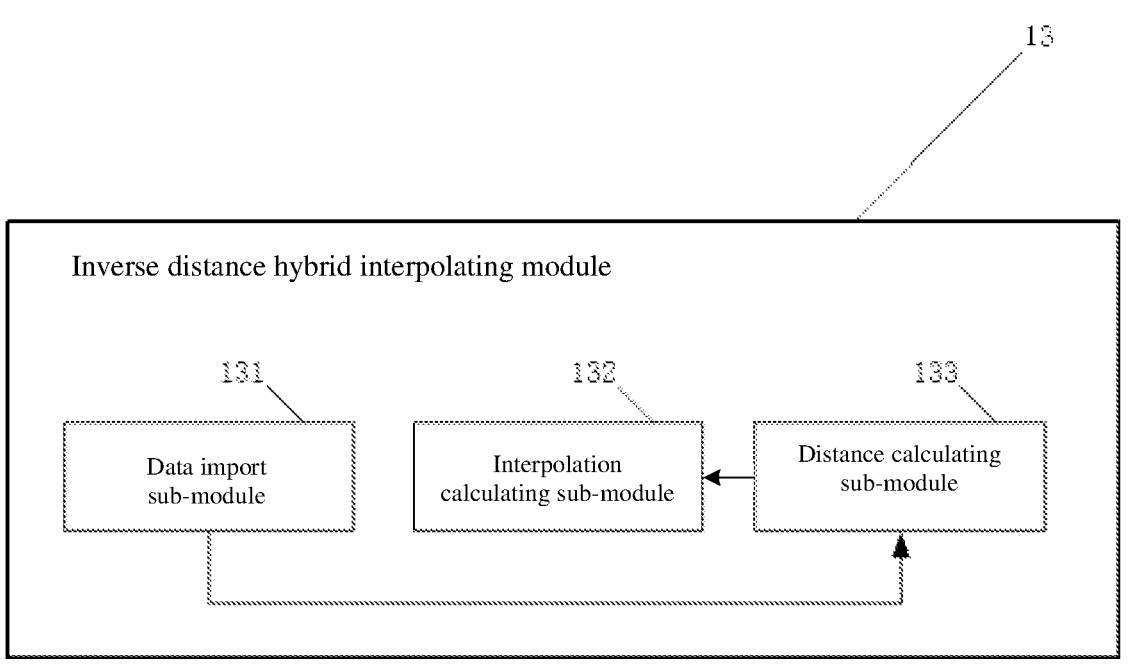
FIG. 14 is an exemplary block diagram of an inverse distance hybrid interpolation module of the data agile inbound technical system shown in FIG. 12.

FIG. 14 is an exemplary block diagram of an inverse distance hybrid interpolation module of the data agile inbound technical system 1 shown in FIG. 12. For example, as shown in FIG. 13, the inverse distance hybrid interpolation module 13 includes a data import sub-module 131, a distance calculating sub-module 133 and an interpolation calculating sub-module 132.

For example, the data import sub-module 131, the distance calculating sub-module 133 and the interpolation calculating sub-module 132 may be respectively implemented by the second data receiving sub-module, the distance calculating sub-module and the interpolation calculating sub-module shown in FIG. 10. Therefore, the example shown in FIG. 10 may be referred to for specific implementation modes of the data import sub-module 131, the distance calculating sub-module 133 and the interpolation calculating sub-module 132 as described above.

For example, by using the inverse distance interpolation calculation mechanism, by performing interpolation calculation according to the inverse distance in the grouped patient, the missing portion of the input mobile data may be interpolated and supplemented, for example, streaming data with different frequencies. For example, a distance damping factor is also introduced in interpolation calculation, which may effectively improve credibility of interpolation calculation.

For example, by using a hybrid distance calculation mechanism, and calculating the nominal distance (e.g., definition of distance includes actual distance, geodesic distance, etc.) in combination with patient baseline information and historical data, customization may be performed according to actual needs, and finally the result is input into inverse distance interpolation calculation.

Figure 15:
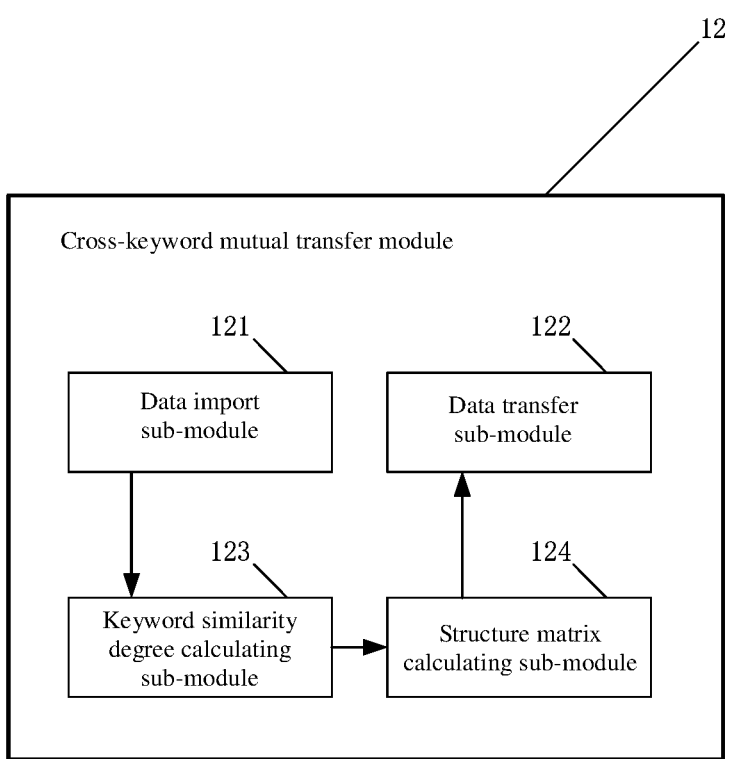
FIG. 15 is an exemplary block diagram of a cross-keyword mutual transfer module of the data agile inbound technical system shown in FIG. 12.

FIG. 15 is an exemplary block diagram of a cross-keyword mutual transfer module of the data agile inbound technical system 1 shown in FIG. 12. For example, as shown in FIG. 14, the cross-keyword mutual transfer module 12 includes a data import sub-module 121, a keyword similarity degree calculating sub-module 123, a structure matrix calculating sub-module 124, and a data transfer sub-module 122.

For example, the data import sub-module 121, the keyword similarity degree calculating sub-module 123+the structure matrix calculating sub-module 124 and the data transfer sub-module 122 may be respectively implemented by the first data receiving sub-module, the structural similarity degree calculating sub-module and the transfer sub-module shown in FIG. 3. Therefore, the example shown in FIG. 3 may be referred to for specific implementation modes of the data import sub-module 121, the keyword similarity degree calculating sub-module 123+the structure matrix calculating sub-module 124 and the data transfer sub-module 122.

For example, the above-described mobile data agile inbound solution may implement data preprocessing on the raw data and implement agile inbound on the basis of collecting returned data of various intelligent devices carried by patients with the sub-type of disease, which provides a complete, standardized and tidy high-quality data source, and facilitates further analysis on the basis of the data of the type of disease.

For example, the COPD baseline scoring module adopts a quantitative scoring mechanism based on data tables, which is formulated based on existing clinical observation, and is simple in criteria, uniform and very easy to implement, and meanwhile, may be flexibly modified according to medical practice criteria in various regions, so as to improve logic stability and extensibility of the solution. According to the scoring mechanism, the inbound patient data may be merged and grouped by simple query, which is favorable for efficient distributed execution of subsequent preprocessing tasks.

For example, the inverse distance hybrid interpolation module adopts a nominal distance distribution mechanism, which may obtain credibility of interpolation based on adjacent patient data, on the basis of patient grouping, according to spatiotemporal correlation between collection location and collection time of mobile data, and may perform hybrid interpolation based on baseline data according to magnitude and inverse relationship of values thereof. According to the interpolation module, missing data values may be filled, and data of different frequencies may be interpolated to obtain inbound patient data of a same frequency, which may greatly improve granularity of subsequent data analysis.

For example, the cross-keyword mutual transfer module adopts a keyword similarity degree matrix conversion mechanism. After patient mobile data is transmitted and arrives, by unpacking the obtained data, list data may be obtained; and then a similarity degree matrix is calculated according to the similarity degree of header keywords of the list data and structural characteristics of the type of the data. When the device keyword used by the patient is not consistent with keywords of other patients, according to the module, the data may be smoothly converted to a same storage form to ensure uniformity of the inbound patient data.

At least one embodiment of the present disclosure provides a data processing method, including: performing data processing on device-related data originating from a device associated with a health managing apparatus.

Figure 16:
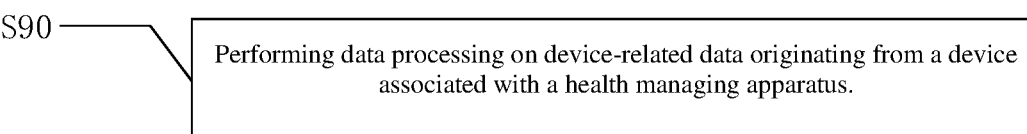
FIG. 16 is an exemplary flow chart of a data processing method provided by at least one embodiment of the present disclosure.

FIG. 16 is an exemplary flow chart of a data processing method provided by at least one embodiment of the present disclosure.

For example, as shown in FIG. 16, the data processing method includes step S90 below:

Step S90: performing data processing on device-related data originating from a device associated with a health managing apparatus.

For example, the processed data is supplied to a memory or a database associated with the health managing apparatus.

In a first example, step S90 includes step S911 and step S912 below.

Step S911: based on information of a first group of keywords involved in template data and information of a second group of keywords involved in the device-related data, acquiring a structural similarity degree between the first group of keywords and the second group of keywords.

Step S912: transferring at least a portion of the device-related data into the template data based on the structural similarity degree.

For example, step S911 and step S912 may be executed sequentially.

For example, the structural similarity degree between the first group of keywords and the second group of keywords includes a similarity degree between an eigenvector of each keyword of the first group of keywords and an eigenvector of each keyword of the second group of keywords. For example, the eigenvectors of the first group of keywords are $v_1, v_2, \ldots, v_m$, the eigenvectors of the second group of keywords are $u_1, u_2, \ldots u_b$, m is the number of keywords in the first group of keywords, and b is the number of keywords in the second group of keywords.

For example, step S911 includes: acquiring the structural similarity degree between the first group of keywords and the second group of keywords by calculating a similarity degree matrix S; the similarity degree matrix S satisfying an expression below.

$$S = \begin{bmatrix} u_1v_1 & u_1v_2 & \ldots & u_1v_m \\ u_2v_1 & u_2v_2 & & u_2v_m \\ \vdots & \vdots & \ddots & \vdots \\ u_bv_1 & u_bv_2 & \ldots & u_bv_m \end{bmatrix}$$

For example, step S912 includes step S9121 to step S9123 below.

Step S9121: taking a similarity degree between an eigenvector of each keyword of the second group of keywords and an eigenvector of each keyword of the first group of keywords whose value is greater than a preset similarity degree threshold as a relevant similarity degree.

Step S9122: taking a keyword belonging to the second group of keywords in two keywords corresponding to each relevant similarity degree as a first keyword, and taking a keyword belonging to the first group of keywords in the two keywords corresponding to each relevant similarity degree as a second keyword.

Step S9123: associating the data associated with the first keyword in the device-related data with the second keyword involved in the template data.

For example, step S9121, step S9122, and step S9123 may be executed sequentially.

For example, in the first example, step S90 further includes step S913 below.

Step S913: receiving information of the first group of keywords involved in the template data and the device-related data. For example, step S913 may be executed before step S911.

For example, the information of the first group of keywords includes an eigenvector of each keyword of the first group of keywords; the information of the second group of keywords includes an eigenvector of each keyword of the second group of keywords.

For example, in the first example, step S90 further includes step S914 and step S915 below.

Step S914: extracting the second group of keywords and hierarchical information of each keyword of the second group of keywords in the device-related data from the device-related data.

Step S915: generating an eigenvector of each keyword of the second group of keywords based on the second group of keywords and hierarchical information of each keyword of the second group of keywords in the device-related data.

For example, step S914 and step S915 may be executed sequentially. For example, step S914 and step S915 may be executed after step S913 and at step S911.

For example, step S913, step S914, step S915, step S911, and step S912 may be executed sequentially.

It should be noted that, in the first example, the data processing method is not limited to including step S913.

In an example, the data processing method does not include the above-described step S913, and the data processing method includes receiving information of the first group of keywords involved in the template data and information of the second group of keywords involved in the device-related data; in this case, the data processing method does not include the above-described step S914 and step S915.

In another example, the data processing method does not include the above-described step S913, and the data processing method provided by at least one embodiment of the present disclosure includes receiving the template data and the device-related data; in this case, in addition to step S911, step S912, step S914 and S915, the data processing method further includes step S916 and step S917 below; and step S916 and step S917 may be executed sequentially. For example, step S916 and step S917 may be executed after step S913 and at step S911.

Step S916: extracting the first group of keywords and hierarchical information of each keyword of the first group of keywords in the template data from the template data.

Step S917: generating an eigenvector of each keyword of the first group of keywords based on the first group of keywords and hierarchical information of each keyword of the first group of keywords in the device-related data.

In yet another example, the data processing method does not include the above-described step S913, but includes the step S918 below: receiving the first group of keywords involved in the template data and the hierarchical information of the first group of keywords as well as the second group of keywords involved in the device-related data and the hierarchical information of the second group of keywords; in this case, the data processing method further includes step S915, step S917, step S911 and step S912. For example, step S918, step S915+step S917, step S911 and step S912 may be executed sequentially.

For example, the relevant description of the example shown in FIG. 2 may be referred to for specific implementation modes of step S911 to step S917, and no details will be repeated here.

In the second example, step S90 includes step S921 to step S923 below.

Step S921: receiving information of the object associated with the health managing apparatus.

Step S922: acquiring scores of the object associated with the health managing apparatus on a plurality of scoring items based on the information of the object associated with the health managing apparatus and a look-up table.

Step S923: assigning a group to the object associated with the health managing apparatus based on the scores of the object associated with the health managing apparatus on a plurality of scoring items.

For example, step S921, step S922 and step S923 may be executed sequentially.

For example, step S923 includes step S9231 and step S9232 below. For example, step S9231 and step S9232 may be executed sequentially.

Step S9231: acquiring an overall score of the object associated with the health managing apparatus based on the scores on the plurality of scoring items and weights of the plurality of scoring items.

Step S9232: assigning a group to the object associated with the health managing apparatus based on the overall score.

For example, in step S9231, the acquiring an overall score of the object associated with the health managing apparatus based on the scores on the plurality of scoring items and weights of the plurality of scoring items includes: taking a weighted sum of the scores of the object associated with the health managing apparatus on a plurality of scoring items as the overall score of the object associated with the health managing apparatus.

For example, in step S9232, the assigning a group to the object associated with the health managing apparatus based on the overall score includes: taking the overall score rounded up as a group sequence number of the object associated with the health managing apparatus.

For example, the information of the object associated with the health managing apparatus includes objective information and subjective information; at least a portion of the objective information is acquired through monitoring the object associated with the health managing apparatus by a portable medical device or a wearable medical device; and at least a portion of the subjective information is acquired through queries by a medical worker or an electronic questionnaire filled by the object associated with the health managing apparatus.

For example, with respect to COPD, the plurality of scoring items include: age, gender, Body Mass Index (BMI), systolic blood pressure, diastolic blood pressure, occupational work intensity, the number of exacerbations, the number of hospitalizations, the number of surgical treatments, normal respiratory rate, normal oxyhemoglobin saturation, mental status and exercise status.

For example, in the second example, step S90 further includes step S924 below. For example, step S924 may be executed after step S9231.

Step S924: receiving the overall score of the object associated with the health managing apparatus, and outputting pre-warning information when the overall score of the object associated with the health managing apparatus is greater than the score threshold.

For example, the relevant description of the example shown in FIG. 5 may be referred to for specific implementation modes of step S921 to step S924, and no details will be repeated here.

In the third example, step S90 includes step S931 and step S932 below.

Step S931: receiving an interpolated data set, wherein the interpolated data set comprises at least a portion of data of other objects in a group to which an object corresponding to data to be supplemented belongs.

Step S932: performing interpolation on the interpolated data set to acquire the data to be supplemented.

For example, step S931 and step S932 may be executed sequentially.

For example, in step S932, the performing interpolation on the interpolated data set to acquire the data to be supplemented includes: performing inverse distance interpolation on the interpolated data set at least based on the nominal distance to acquire the data to be supplemented.

For example, in the third example, step S90 further includes step S933 below.

Step S933: calculating a nominal distance between the data to be supplemented and each piece of data in the interpolated data set.

For example, step S933 may be executed before step S932.

For example, in step S933, the calculating a nominal distance between the data to be supplemented and each piece of data in the interpolated data set includes: calculating a nominal distance between the data to be supplemented and each piece of data in the interpolated data set based on a time distance and a geographic distance between the data to be supplemented and each piece of data in the interpolated data set.

For example, in the third example, step S90 further includes step S934 below.

Step S934: receiving time information and geographic location information corresponding to each piece of data in the interpolated data set, as well as time information and geographic location information corresponding to the data to be supplemented.

For example, step S934 may be executed before step S933.

For example, in step S933, the calculating a nominal distance between the data to be supplemented and each piece of data in the interpolated data set includes step S9331 to step S9333 below.

Step S9331: calculating a time distance between the data to be supplemented and each piece of data in the interpolated data set, based on time information corresponding to each piece of data in the interpolated data set and the time information corresponding to the data to be supplemented;

Step S9332: calculating a geographic distance between the data to be supplemented and each piece of data in the interpolated data set, based on geographic information corresponding to each piece of data in the interpolated data set and the geographic information corresponding to the data to be supplemented;

Step S9333: taking a weighted sum of a spatial distance between the data to be supplemented and each piece of data in the interpolated data set and a time distance between the data to be supplemented and each piece of data in the interpolated data set as a nominal distance between the data to be supplemented and each piece of data in the interpolated data set.

For example, step S9331 to step S9333 may be executed in an order of step S9331, step S9332, and step S9333. For another example, step S9331 to step S9333 may be executed in an order of step S9332, step S9331 and step S9333. For another example, step S9331 to step S9333 may be executed in an order of step S9331+step S9332 (i.e., step S9331 and step S9332 being executed simultaneously) and step S9333.

For example, in the third example, step S90 further includes step S935 below.

Step S935: receiving a damping item of the group to which the object corresponding to the data to be supplemented belongs. For example, step S935 is executed before step S932.

For example, in step S932, the performing interpolation on the interpolated data set to acquire the data to be supplemented includes: performing inverse distance interpolation on the interpolated data set based on the nominal distance and the damping item to acquire the data to be supplemented.

For example, in at least one example of the data processing method, the data to be supplemented $x_p$ satisfies an expression below:

$$x_p = \frac{\sum_{i=1}^{n} \frac{x_i}{d_{pi}^{1.5}}}{\sum_{i=1}^{n} \frac{1}{e_k \cdot d_{pi}^{1.5}}}$$

$x_i$ is an i-th piece of data in the interpolated data set, where i is a positive integer greater than or equal to 1 and less than or equal to n; n is a count of pieces of data in the interpolated data set; $d_{pi}$ is a nominal distance between the data to be supplemented $x_p$ and the i-th piece of data $x_i$ in the interpolated data set; $e_k$ is the damping item of the group to which the object corresponding to the data to be supplemented belongs, k is greater than or equal to 1 and less than or equal to t, and t is a group sequence number of a group to which an object associated with the health managing apparatus belongs.

For example, step S931+step S934+step S935 (i.e., step S931, step S934 and step S935 being executed simultaneously), step S933 and step S932 may be executed sequentially. For another example, step S931+step S934 (i.e., step S931 and step S934 being executed simultaneously), step S933, step S935 and step S932 may be executed sequentially. For another example, step S931, step S934, step S933, step S935, and step S932 may be executed sequentially. For another example, step S934, step S931, step S933, step S935 and step S932 may be executed sequentially.

For example, the relevant description of the examples shown in FIG. 9 and FIG. 10 may be referred to for specific implementation modes of step S931 to step S935, and no details will be repeated here.

In the fourth example, step S90 includes step S921 to step S923 and step S931 to step S935 below. For example, step S921 to step S923 are executed before step S931 to step S935.

In the fifth example, step S90 includes step S911 to step S915, step S921 to step S923, and step S931 to step S935 below. For example, steps S921 to step S923 may be executed before step S931 to step S935; step S911 to step S915 may be executed before step S931 to step S935. For example, step S911 to step S915 are executed before step S921 to step S923. For another example, step S911 to step S915 are executed after step S921 to step S923.

In the sixth example, in the fifth example, step S90 includes step S911 to S915 and step S921 to S923 below. For example, step S911 to step S915 may be executed before step S921 to step S923. For another example, step S911 to step S915 may be executed after step S921 to step S923.

For example, in step S90, the performing data processing on device-related data originating from a device associated with a health managing apparatus includes: performing distributed processing on device-related data originating from the device associated with the health managing apparatus.

Figure 17:
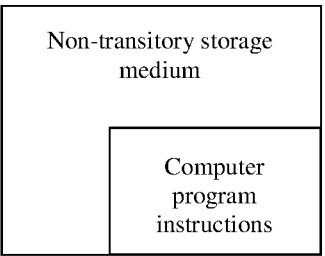
FIG. 17 shows an exemplary block diagram of a non-transitory storage medium provided by at least one embodiment of the present disclosure.

At least one embodiment of the present disclosure further provides a non-transitory storage medium. FIG. 17 shows an exemplary block diagram of a non-transitory storage medium provided by at least one embodiment of the present disclosure. For example, as shown in FIG. 17, the non-transitory storage medium has computer program instructions stored therein; and when the computer program instructions are run by a processor, the computer program instructions cause the process to execute a method comprising: performing data processing on device-related data originating from a device associated with a health managing apparatus.

For example, the non-transitory storage medium may include a Read Only Memory (ROM), a hard disk, a flash memory, or the like. For example, the data processing method provided by at least one embodiment of the present disclosure may be referred to for a specific implementation method of performing data processing on the device-related data originating from the device associated with the health managing apparatus, and no details will be repeated here.

Figure 18:
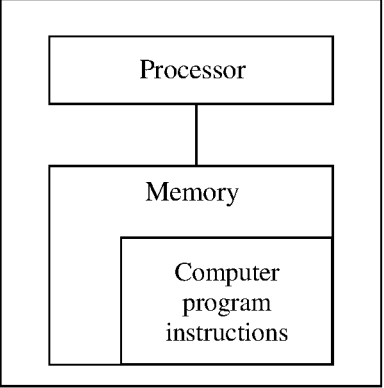
FIG. 18 shows an exemplary block diagram of another data processing apparatus provided by at least one embodiment of the present disclosure.

At least one embodiment of the present disclosure further provides another data processing apparatus. FIG. 18 shows an exemplary block diagram of another data processing apparatus provided by at least one embodiment of the present disclosure. For example, as shown in FIG. 18, the another data processing apparatus includes: a processor and a memory. The memory has computer program instructions suitable for execution by the processor stored therein; and when the computer program instructions are run by the processor, the computer program instructions cause the process to execute a method comprising: performing data processing on device-related data originating from a device associated with a health managing apparatus.

For example, the processor is, for example, a Central Processing Unit (CPU) or other form of processing unit with a data processing capability and/or an instruction execution capability; for example, the processor may be implemented as a general-purpose processor, and also a single-chip micro-computer, a micro-processor, a digital signal processor, a dedicated image processing chip, or a field programmable gate array, or the like. The memory may include, for example, a volatile memory and/or a non-volatile memory, and may include, for example, a Read-Only Memory (ROM), a hard disk, a flash memory, or the like. Correspondingly, the memory may be implemented as one or more computer program products, and the computer program products may include various forms of computer-readable storage media; and one or more computer program instructions may be stored on the computer-readable storage media. The processor may run the program instructions, to implement desired functions. The memory may also store various other application programs and various data, as well as various data used and/or generated by the application programs.

For example, the data processing method provided by at least one embodiment of the present disclosure may be referred to for a specific implementation method for performing data processing on the device-related data originating from the device associated with the health managing apparatus, and no details will be repeated here.

Figure 19:
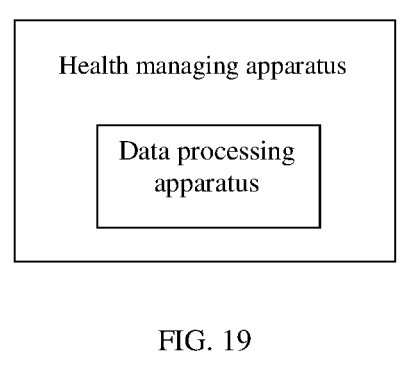

At least one embodiment of the present disclosure further provides a health managing apparatus, which includes any one data processing apparatus provided by at least one embodiment of the present disclosure. FIG. 19 is an exemplary block diagram of a health managing apparatus provided by at least one embodiment of the present disclosure. As shown in FIG. 19, the health managing apparatus includes any one data processing apparatus provided by at least one embodiment of the present disclosure. For example, the relevant embodiments may be referred to for a specific implementation mode of the data processing apparatus, and no details will be repeated here.

Although the present disclosure has been described in detail above with general description and specific implementation, but on the basis of the present disclosure, some modifications or improvements can be made to it, which is important to those skilled in the art. Obvious. Therefore, these modifications or improvements made without departing from the spirit of the present disclosure fall within the scope of the claimed protection of the present disclosure.

The above description is only an exemplary embodiment of the present disclosure, and is not intended to limit the protection scope of the present disclosure, which is determined by the appended claims.

What is claimed is:

1. A data processing method, comprising:
   receiving device-related data uploaded through a network and collected and generated by a plurality of devices associated with a health managing apparatus, wherein a format of the device-related data is in a non-standardized data format and the non-standardized data format is different from a predetermined data format;
   determining a group corresponding to an object associated with the health managing apparatus, wherein the group is used to indicate a severity of disease of the object, an importance level of data of the object, or a query frequency of the data of the object;
   storing the device-related data corresponding to the object in a memory of a corresponding level based on the group, wherein in response to a higher level of the group, the corresponding device-related data is stored in a memory with a faster read-write speed;
   reading non-standardized device-related data from memories of different levels, wherein the non-standardized device-related data stored in the memory with the faster read-write speed is read with priority;
   converting, by a data processing apparatus, the non-standardized device-related data into data with the predetermined data format based on template data, wherein the predetermined data format comprises a data format used by a memory associated with the health managing apparatus, or the predetermined data format comprises a data format used by first devices among the plurality of devices, and a proportion of the first devices in the plurality of devices exceeds a predetermined value, the template data has the predetermined data format but does not comprise a specific numerical value; and
   directly or indirectly storing the data with the predetermined data format to the memory associated with the health managing apparatus.

2. The data processing method according to claim 1, wherein the converting the non-standardized device-related data into data with the predetermined data format comprises:
   based on information of a first group of keywords involved in the template data and information of a second group of keywords involved in the device-related data, acquiring a structural similarity degree between the first group of keywords and the second group of keywords; and transferring at least a portion of the device-related data into the template data based on the structural similarity degree.

3. The data processing method according to claim 2, wherein the converting the non-standardized device-related data into data with the predetermined data format further comprises:

receiving the device-related data and the information of the first group of keywords involved in the template data, wherein the information of the first group of keywords comprises an eigenvector of each keyword of the first group of keywords, and the information of the second group of keywords comprises an eigenvector of each keyword of the second group of keywords;

extracting the second group of keywords and hierarchical information of each keyword of the second group of keywords in the device-related data from the device-related data; and for each keyword of the second group of keywords, generating an eigenvector of the keyword of the second group of keywords based on the second group of keywords and hierarchical information of the keyword of the second group of keywords in the device-related data.

4. The data processing method according to claim 3, wherein the structural similarity degree between the first group of keywords and the second group of keywords comprises a similarity degree between an eigenvector of each keyword of the first group of keywords and an eigenvector of each keyword of the second group of keywords.

5. The data processing method according to claim 4, wherein the acquiring the structural similarity degree between the first group of keywords and the second group of keywords comprises:

acquiring the structural similarity degree between the first group of keywords and the second group of keywords by calculating a similarity degree matrix S; and the similarity degree matrix S satisfying an expression below:

$$S = \begin{bmatrix} u_1 v_1 & u_1 v_2 & \dots & u_1 v_m \\ u_2 v_1 & u_2 v_2 & & u_2 v_m \\ \vdots & \vdots & \ddots & \vdots \\ u_b v_1 & u_b v_2 & \dots & u_b v_m \end{bmatrix}$$

wherein $v_1, v_2, \dots, v_m$ are eigenvectors of the first group of keywords, $u_1, u_2, \dots, u_b$ are eigenvectors of the second group of keywords, m is a count of keywords in the first group of keywords, and b is a count of keywords in the second group of keywords.

6. The data processing method according to claim 3, wherein the transferring at least the portion of the device-related data into the template data based on the structural similarity degree comprises:

taking a similarity degree between an eigenvector of each keyword of the second group of keywords and an eigenvector of each keyword of the first group of keywords greater than a preset similarity degree threshold as a relevant similarity degree to obtain at least one relevant similarity degree;

for each relevant similarity degree of the at least one relevant similarity degree, taking a keyword belonging to the second group of keywords in two keywords corresponding to the relevant similarity degree as a first keyword, and taking a keyword belonging to the first group of keywords in the two keywords corresponding to the relevant similarity degree as a second keyword; and associating data associated with the first keyword in the device-related data with the second keyword involved in the template data.

7. The data processing method according to claim 1, wherein the converting the non-standardized device-related data into data with the predetermined data format further comprises:

receiving an interpolated data set, wherein the interpolated data set comprises at least a portion of data of other objects in a group to which an object corresponding to data to be supplemented belongs;

performing interpolation on the interpolated data set to acquire the data to be supplemented; and calculating a nominal distance between the data to be supplemented and each piece of data in the interpolated data set to obtain at least one nominal distance, wherein the performing the interpolation on the interpolated data set to acquire the data to be supplemented comprises:

performing inverse distance interpolation on the interpolated data set at least based on the at least one nominal distance to acquire the data to be supplemented.

8. The data processing method according to claim 7, wherein the calculating the nominal distance between the data to be supplemented and each piece of data in the interpolated data set comprises:

calculating a nominal distance between the data to be supplemented and each piece of data in the interpolated data set, based on a time distance and a geographic distance between the data to be supplemented and each piece of data in the interpolated data set.

9. The data processing method according to claim 8, further comprising:

receiving time information and geographic location information corresponding to each piece of data in the interpolated data set, as well as time information and geographic location information corresponding to the data to be supplemented, wherein the calculating a nominal distance between the data to be supplemented and each piece of data in the interpolated data set, comprises:

for each piece of data in the interpolated data set:

calculating a time distance between the data to be supplemented and the piece of data in the interpolated data set, based on time information corresponding to the piece of data in the interpolated data set and the time information corresponding to the data to be supplemented;

calculating a geographic distance between the data to be supplemented and the piece of data in the interpolated data set, based on geographic information corresponding to the piece of data in the interpolated data set and geographic information corresponding to the data to be supplemented; and taking a weighted sum of the geographic distance between the data to be supplemented and the piece of data in the interpolated data set and the time distance between the data to be supplemented and the piece of data in the interpolated data set as a nominal distance between the data to be supplemented and the piece of data in the interpolated data set.

10. The data processing method according to claim 7, further comprising:

receiving a damping item of the group to which the object corresponding to the data to be supplemented belongs, wherein the performing the interpolation on the interpolated data set to acquire the data to be supplemented, comprises:

performing inverse distance interpolation on the interpolated data set based on the at least one nominal distance and the damping item to acquire the data to be supplemented.

11. The data processing method according to claim 10, wherein the data to be supplemented $x_p$ satisfies an expression below:

$$x_p = \frac{\sum_{i=1}^{n} \frac{x_i}{d_{pi}^{1.5}}}{\sum_{k=1}^{n} \frac{1}{e_k \cdot d_{pi}^{1.5}}}$$

wherein $x_i$ is an i-th piece of data in the interpolated data set, where i is a positive integer greater than or equal to 1 and less than or equal to n;

n is a count of pieces of data in the interpolated data set;

$d_{pi}$ is a nominal distance between the data to be supplemented $x_p$ and the i-th piece of data $x_i$ in the interpolated data set;

$e_k$ is the damping item of the group to which the object corresponding to the data to be supplemented belongs, k is greater than or equal to 1 and less than or equal to t, and t is a group sequence number of a group to which an object associated with the health managing apparatus belongs.

12. The data processing method according to claim 1, further comprising:

receiving information of the object associated with the health managing apparatus;

acquiring scores of the object associated with the health managing apparatus on a plurality of scoring items based on the information of the object associated with the health managing apparatus and a look-up table; and assigning a group to the object associated with the health managing apparatus based on the scores of the object associated with the health managing apparatus on the plurality of scoring items.

13. The data processing method according to claim 12, wherein the assigning the group to the object associated with the health managing apparatus based on the scores of the object associated with the health managing apparatus on the plurality of scoring items comprises:

acquiring an overall score of the object associated with the health managing apparatus based on the scores on the plurality of scoring items and weights of the plurality of scoring items; and assigning the group to the object associated with the health managing apparatus based on the overall score.

14. The data processing method according to claim 13, wherein the acquiring the overall score of the object associated with the health managing apparatus based on the scores on the plurality of scoring items and weights of the plurality of scoring items comprises:

taking a weighted sum of the scores of the object associated with the health managing apparatus on the plurality of scoring items as the overall score of the object associated with the health managing apparatus, and wherein the assigning the group to the object associated with the health managing apparatus based on the overall score comprises:

taking the overall score rounded up as a group sequence number of the object associated with the health managing apparatus.

15. The data processing method according to claim 13, wherein the information of the object associated with the health managing apparatus comprises objective information and subjective information;

at least a portion of the objective information is acquired through monitoring the object associated with the health managing apparatus by a portable medical device or a wearable medical device;

at least a portion of the subjective information is acquired through queries by a medical worker or an electronic questionnaire filled by the object associated with the health managing apparatus; and the plurality of scoring items comprise: age, gender, Body Mass Index, systolic blood pressure, diastolic blood pressure, occupational work intensity, a count of exacerbations, a count of hospitalizations, a count of surgical treatments, normal respiratory rate, normal oxyhemoglobin saturation, mental status, and exercise status.

16. The data processing method according to claim 15, further comprising:

receiving the overall score of the object associated with the health managing apparatus, and outputting prewarning information in a case where the overall score of the object associated with the health managing apparatus is greater than a score threshold.

17. A data processing apparatus, comprising:

a processor and a memory, wherein the memory stores computer program instructions suitable for execution by the processor; and in a case where the computer program instructions are run by the processor, causing the processor to execute a method comprising:

receiving device-related data uploaded through a network and collected and generated by a plurality of devices associated with a health managing apparatus, wherein a format of the device-related data is in a non-standardized data format and the non-standardized data format is different from a predetermined data format;

determining a group corresponding to an object associated with the health managing apparatus, wherein the group is used to indicate a severity of disease of the object, an importance level of data of the object, or a query frequency of the data of the object;

storing the device-related data corresponding to the object in a memory of a corresponding level based on the group, wherein in response to a higher level of the group, the corresponding device-related data is stored in a memory with a faster read-write speed;

reading non-standardized device-related data from memories of different levels, wherein the non-standardized device-related data stored in the memory with the faster read-write speed is read with priority;

converting, by the data processing apparatus, the non-standardized device-related data into data with the predetermined data format based on template data, wherein the predetermined data format comprises a data format used by a memory associated with the health managing apparatus, or the predetermined data format comprises a data format used by first devices among the plurality of devices, and a proportion of the first devices in the plurality of devices exceeds a predetermined value, the template data has the predetermined data format but does not comprise a specific numerical value; and directly or indirectly storing the data with the predetermined data format to the memory associated with the health managing apparatus.

18. A health managing apparatus, comprising the data processing apparatus according to claim 17.

19. A non-transitory storage medium, having computer program instructions stored thereon, wherein when the computer program instructions are run by a processor, the computer program instructions cause the process to execute a method comprising:

receiving device-related data uploaded through a network and collected and generated by a plurality of devices associated with a health managing apparatus, wherein a format of the device-related data is in a non-standardized data format and the non-standardized data format is different from a predetermined data format;

determining a group corresponding to an object associated with the health managing apparatus, wherein the group is used to indicate a severity of disease of the object, an importance level of data of the object, or a query frequency of the data of the object;

storing the device-related data corresponding to the object in a memory of a corresponding level based on the group, wherein in response to a higher level of the group, the corresponding device-related data is stored in a memory with a faster read-write speed;

reading non-standardized device-related data from memories of different levels, wherein the non-standardized device-related data stored in the memory with the faster read-write speed is read with priority;

converting, by a data processing apparatus, the non-standardized device-related data into data with the predetermined data format based on template data, wherein the predetermined data format comprises a data format used by a memory associated with the health managing apparatus, or the predetermined data format comprises a data format used by first devices among the plurality of devices, and a proportion of the first devices in the plurality of devices exceeds a predetermined value, the template data has the predetermined data format but does not comprise a specific numerical value; and directly or indirectly storing the data with the predetermined data format to the memory associated with the health managing apparatus.

20. A data processing apparatus, comprising a data processing circuit, wherein the data processing circuit is configured to execute the data processing method according to claim 1.

* * * * *